United States Patent
Choudhary et al.

(10) Patent No.: US 9,641,469 B2
(45) Date of Patent: *May 2, 2017

(54) USER MESSAGING BASED ON CHANGES IN TRACKED ACTIVITY METRICS

(71) Applicant: Fitbit, Inc., San Francisco, CA (US)

(72) Inventors: Nichiketa Choudhary, San Francisco, CA (US); Timothy Roberts, San Francisco, CA (US); David Knight, San Francisco, CA (US)

(73) Assignee: Fitbit, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/099,325

(22) Filed: Apr. 14, 2016

(65) Prior Publication Data

US 2016/0234143 A1    Aug. 11, 2016

Related U.S. Application Data

(63) Continuation of application No. 14/445,033, filed on Jul. 28, 2014, now Pat. No. 9,344,546, which is a
(Continued)

(51) Int. Cl.
*H04L 12/58* (2006.01)
*H04M 1/725* (2006.01)
(Continued)

(52) U.S. Cl.
CPC .......... *H04L 51/046* (2013.01); *A61B 5/0022* (2013.01); *A61B 5/1118* (2013.01);
(Continued)

(58) Field of Classification Search
CPC ....... A61B 5/00; A61B 5/7246; A61B 5/6838; A61B 5/1118; A61B 5/681; A61B 5/222;
(Continued)

(56) References Cited

U.S. PATENT DOCUMENTS 2,717,736 A    9/1955    Schlesinger
2,827,309 A    3/1958    Fred
(Continued)

FOREIGN PATENT DOCUMENTS

CN    100998921    7/2007
CN    102598086    7/2007
(Continued)

OTHER PUBLICATIONS

Chandrasekar et al., Aug. 28-Sep. 1, 2012, Plug-and-Play, Single-Chip Photoplethysmography, 34th Annual International Conference of the IEEE EMBS, San Diego, California USA, 4 pages.
(Continued)

*Primary Examiner* — Le H Luu
(74) *Attorney, Agent, or Firm* — Knobbe, Martens, Olson & Bear, LLP

(57) ABSTRACT

A system comprising at least one server computer having at least one processor programmed to: receive, over a network, activity data of a first user measured by an activity monitoring device; process the activity data of the first user to update a value of an activity metric for the first user; responsive to updating the value of the activity metric for the first user, identify a change in an inequality relationship between the value of the activity metric for the first user and a value of the activity metric for a second user; and, responsive to identifying the change in the inequality relationship, trigger, over the network, a first user device to prompt the first user to generate a message to the second user for display on a second user device.

30 Claims, 22 Drawing Sheets

Related U.S. Application Data continuation-in-part of application No. 14/271,412, filed on May 6, 2014, now Pat. No. 9,031,812.

(51) Int. Cl.

| | | |
|---|---|---|
| G08B 3/10 | (2006.01) | |
| G08B 5/36 | (2006.01) | |
| G08B 6/00 | (2006.01) | |
| A61B 5/22 | (2006.01) | |
| A61B 5/00 | (2006.01) | |
| G01C 22/00 | (2006.01) | |
| G06F 3/041 | (2006.01) | |
| G06F 15/00 | (2006.01) | |
| G06F 19/00 | (2011.01) | |
| H04L 29/06 | (2006.01) | |
| H04L 29/08 | (2006.01) | |
| G08B 21/18 | (2006.01) | |
| G06F 17/24 | (2006.01) | |
| G06F 17/30 | (2006.01) | |
| A61B 5/0205 | (2006.01) | |
| A61B 5/021 | (2006.01) | |
| A61B 5/024 | (2006.01) | |
| A61B 5/11 | (2006.01) | |
| A61B 5/1455 | (2006.01) | |

(52) U.S. Cl.
CPC .............. *A61B 5/22* (2013.01); *A61B 5/743* (2013.01); *G01C 22/006* (2013.01); *G06F 3/041* (2013.01); *G06F 15/00* (2013.01); *G06F 17/248* (2013.01); *G06F 17/3053* (2013.01); *G06F 19/3481* (2013.01); *G08B 3/10* (2013.01); *G08B 5/36* (2013.01); *G08B 6/00* (2013.01); *G08B 21/182* (2013.01); *H04L 51/00* (2013.01); *H04L 51/32* (2013.01); *H04L 65/403* (2013.01); *H04L 67/22* (2013.01); *H04L 67/26* (2013.01); *H04M 1/72519* (2013.01); *A61B 5/021* (2013.01); *A61B 5/02055* (2013.01); *A61B 5/02405* (2013.01); *A61B 5/1112* (2013.01); *A61B 5/1123* (2013.01); *A61B 5/14551* (2013.01); *A61B 5/222* (2013.01); *A61B 5/4809* (2013.01); *A61B 5/4812* (2013.01); *A61B 5/4815* (2013.01); *A61B 5/681* (2013.01); *A61B 5/6838* (2013.01); *A61B 2560/0214* (2013.01); *A61B 2560/0242* (2013.01); *A61B 2562/0219* (2013.01)

(58) Field of Classification Search
CPC ...... G04F 10/00; G06F 19/3418; G06F 17/00; G10H 1/40; G06Q 90/00; A63B 71/06; G01S 5/00; G09B 19/00; H04L 51/32; H04L 51/00; G01C 22/006
See application file for complete search history.

(56) References Cited

U.S. PATENT DOCUMENTS

| | | |
|---|---|---|
| 2,883,255 A | 4/1959 | Anderson |
| 3,163,856 A | 12/1964 | Kirby |
| 3,250,270 A | 5/1966 | Walter |
| 3,522,383 A | 7/1970 | Chang |
| 3,918,658 A | 11/1975 | Beller |
| 4,192,000 A | 3/1980 | Lipsey |
| 4,244,020 A | 1/1981 | Ratcliff |
| 4,281,663 A | 8/1981 | Pringle |
| 4,284,849 A | 8/1981 | Anderson et al. |
| 4,312,358 A | 1/1982 | Barney |
| 4,367,752 A | 1/1983 | Jimenez et al. |
| 4,390,922 A | 6/1983 | Pelliccia |
| 4,407,295 A | 10/1983 | Steuer et al. |
| 4,425,921 A | 1/1984 | Fujisaki et al. |
| 4,575,804 A | 3/1986 | Ratcliff |
| 4,578,769 A | 3/1986 | Frederick |
| 4,617,525 A | 10/1986 | Lloyd |
| 4,887,249 A | 12/1989 | Thinesen |
| 4,977,509 A | 12/1990 | Pitchford et al. |
| 5,058,427 A | 10/1991 | Brandt |
| 5,224,059 A | 6/1993 | Nitta et al. |
| 5,295,085 A | 3/1994 | Hoffacker |
| 5,323,650 A | 6/1994 | Fullen et al. |
| 5,446,705 A | 8/1995 | Haas et al. |
| 5,456,648 A | 10/1995 | Edinburg et al. |
| 5,553,296 A | 9/1996 | Forrest et al. |
| 5,583,776 A | 12/1996 | Levi et al. |
| 5,645,509 A | 7/1997 | Brewer et al. |
| 5,671,162 A | 9/1997 | Werbin |
| 5,704,350 A | 1/1998 | Williams, III |
| 5,724,265 A | 3/1998 | Hutchings |
| 5,890,128 A | 3/1999 | Diaz et al. |
| 5,891,042 A | 4/1999 | Sham et al. |
| 5,894,454 A | 4/1999 | Kondo |
| 5,899,963 A | 5/1999 | Hutchings |
| 5,947,868 A | 9/1999 | Dugan |
| 5,955,667 A | 9/1999 | Fyfe |
| 5,976,083 A | 11/1999 | Richardson et al. |
| 6,018,705 A | 1/2000 | Gaudet et al. |
| 6,077,193 A | 6/2000 | Buhler et al. |
| 6,085,248 A | 7/2000 | Sambamurthy et al. |
| 6,129,686 A | 10/2000 | Friedman |
| 6,145,389 A | 11/2000 | Ebeling et al. |
| 6,183,425 B1 | 2/2001 | Whalen et al. |
| 6,213,872 B1 | 4/2001 | Harada et al. |
| 6,241,684 B1 | 6/2001 | Amano et al. |
| 6,287,262 B1 | 9/2001 | Amano et al. |
| 6,301,964 B1 | 10/2001 | Fyfe et al. |
| 6,302,789 B2 | 10/2001 | Harada et al. |
| 6,305,221 B1 | 10/2001 | Hutchings |
| 6,309,360 B1 | 10/2001 | Mault |
| 6,469,639 B2 | 10/2002 | Tanenhaus et al. |
| 6,478,736 B1 | 11/2002 | Mault |
| 6,513,381 B2 | 2/2003 | Fyfe et al. |
| 6,513,532 B2 | 2/2003 | Mault et al. |
| 6,527,711 B1 | 3/2003 | Stivoric et al. |
| 6,529,827 B1 | 3/2003 | Beason et al. |
| 6,558,335 B1 | 5/2003 | Thede |
| 6,561,951 B2 | 5/2003 | Cannon et al. |
| 6,571,200 B1 | 5/2003 | Mault |
| 6,585,622 B1 | 7/2003 | Shum et al. |
| 6,607,493 B2 | 8/2003 | Song |
| 6,620,078 B2 | 9/2003 | Pfeffer |
| 6,678,629 B2 | 1/2004 | Tsuji |
| 6,699,188 B2 | 3/2004 | Wessel |
| 6,761,064 B2 | 7/2004 | Tsuji |
| 6,790,178 B1 | 9/2004 | Mault et al. |
| 6,808,473 B2 | 10/2004 | Hisano et al. |
| 6,811,516 B1 | 11/2004 | Dugan |
| 6,813,582 B2 | 11/2004 | Levi et al. |
| 6,813,931 B2 | 11/2004 | Yadav et al. |
| 6,856,938 B2 | 2/2005 | Kurtz |
| 6,862,575 B1 | 3/2005 | Anttila et al. |
| 7,041,032 B1 | 5/2006 | Calvano |
| 7,062,225 B2 | 6/2006 | White |
| 7,133,690 B2 | 11/2006 | Ranta-Aho et al. |
| 7,162,368 B2 | 1/2007 | Levi et al. |
| 7,171,331 B2 | 1/2007 | Vock et al. |
| 7,200,517 B2 | 4/2007 | Darley et al. |
| 7,246,033 B1 | 7/2007 | Kudo |
| 7,261,690 B2 | 8/2007 | Teller et al. |
| 7,272,982 B2 | 9/2007 | Neuhauser et al. |
| 7,285,090 B2 | 10/2007 | Stivoric et al. |
| 7,373,820 B1 | 5/2008 | James |
| 7,443,292 B2 | 10/2008 | Jensen et al. |
| 7,457,724 B2 | 11/2008 | Vock et al. |
| 7,467,060 B2 | 12/2008 | Kulach et al. |
| 7,502,643 B2 | 3/2009 | Farringdon et al. |
| 7,505,865 B2 | 3/2009 | Ohkubo et al. |
| 7,539,532 B2 | 5/2009 | Tran |

(56) References Cited

U.S. PATENT DOCUMENTS

| | | |
|---|---|---|
| 7,558,622 B2 | 7/2009 | Tran |
| 7,559,877 B2 | 7/2009 | Parks et al. |
| 7,653,508 B1 | 1/2010 | Kahn et al. |
| 7,690,556 B1 | 4/2010 | Kahn et al. |
| 7,713,173 B2 | 5/2010 | Shin et al. |
| 7,762,952 B2 | 7/2010 | Lee et al. |
| 7,771,320 B2 | 8/2010 | Riley et al. |
| 7,774,156 B2 | 8/2010 | Niva et al. |
| 7,789,802 B2 | 9/2010 | Lee et al. |
| 7,805,150 B2 | 9/2010 | Graham |
| 7,881,902 B1 | 2/2011 | Kahn et al. |
| 7,927,253 B2 | 4/2011 | Vincent et al. |
| 7,983,876 B2 | 7/2011 | Vock et al. |
| 8,028,443 B2 | 10/2011 | Case, Jr. |
| 8,055,469 B2 | 11/2011 | Kulach et al. |
| 8,099,318 B2 | 1/2012 | Moukas et al. |
| 8,132,037 B2 | 3/2012 | Fehr et al. |
| 8,177,260 B2 | 5/2012 | Tropper et al. |
| 8,180,591 B2 | 5/2012 | Yuen et al. |
| 8,180,592 B2 | 5/2012 | Yuen et al. |
| 8,270,297 B2 | 9/2012 | Akasaka et al. |
| 8,311,769 B2 | 11/2012 | Yuen et al. |
| 8,311,770 B2 | 11/2012 | Yuen et al. |
| 8,386,008 B2 | 2/2013 | Yuen et al. |
| 8,437,980 B2 | 5/2013 | Yuen et al. |
| 8,462,591 B1 | 6/2013 | Marhaben |
| 8,463,576 B2 | 6/2013 | Yuen et al. |
| 8,463,577 B2 | 6/2013 | Yuen et al. |
| 8,533,269 B2 | 9/2013 | Brown |
| 8,533,620 B2 | 9/2013 | Hoffman et al. |
| 8,543,185 B2 | 9/2013 | Yuen et al. |
| 8,543,351 B2 | 9/2013 | Yuen et al. |
| 8,548,770 B2 | 10/2013 | Yuen et al. |
| 8,562,489 B2 | 10/2013 | Burton et al. |
| 8,583,402 B2 | 11/2013 | Yuen et al. |
| 8,597,093 B2 | 12/2013 | Engelberg et al. |
| 8,615,377 B1 | 12/2013 | Yuen |
| 8,634,796 B2 | 1/2014 | Johnson |
| 8,670,953 B2 | 3/2014 | Yuen et al. |
| 8,684,900 B2 | 4/2014 | Tran |
| 8,690,578 B1 * | 4/2014 | Nusbaum ............... G09B 19/00 128/905 |
| 8,734,296 B1 | 5/2014 | Brumback |
| 8,738,321 B2 | 5/2014 | Yuen et al. |
| 8,738,323 B2 | 5/2014 | Yuen et al. |
| 8,744,803 B2 | 6/2014 | Park et al. |
| 8,762,101 B2 | 6/2014 | Yuen et al. |
| 8,764,651 B2 | 7/2014 | Tran |
| 8,847,988 B2 | 9/2014 | Geisner et al. |
| 8,968,195 B2 | 3/2015 | Tran |
| 9,389,057 B2 | 7/2016 | Meschter |
| 9,409,052 B2 | 8/2016 | Werner |
| 9,420,083 B2 | 8/2016 | Roberts |
| 2001/0049470 A1 | 12/2001 | Mault |
| 2001/0055242 A1 | 12/2001 | Deshmukh et al. |
| 2002/0013717 A1 | 1/2002 | Ando et al. |
| 2002/0019585 A1 | 2/2002 | Dickenson |
| 2002/0077219 A1 | 6/2002 | Cohen et al. |
| 2002/0082144 A1 | 6/2002 | Pfeffer |
| 2002/0087264 A1 | 7/2002 | Hills et al. |
| 2002/0109600 A1 | 8/2002 | Mault et al. |
| 2002/0178060 A1 | 11/2002 | Sheehan |
| 2002/0198776 A1 | 12/2002 | Nara et al. |
| 2003/0018523 A1 | 1/2003 | Rappaport et al. |
| 2003/0050537 A1 | 3/2003 | Wessel |
| 2003/0065561 A1 | 4/2003 | Brown et al. |
| 2003/0131059 A1 | 7/2003 | Brown et al. |
| 2004/0054497 A1 | 3/2004 | Kurtz |
| 2004/0061324 A1 | 4/2004 | Howard |
| 2004/0117963 A1 | 6/2004 | Schneider |
| 2004/0152957 A1 | 8/2004 | Stivoric et al. |
| 2004/0239497 A1 | 12/2004 | Schwartzman et al. |
| 2004/0249299 A1 | 12/2004 | Cobb |
| 2005/0037844 A1 | 2/2005 | Shum et al. |
| 2005/0038679 A1 | 2/2005 | Short |
| 2005/0054938 A1 | 3/2005 | Wehman et al. |
| 2005/0102172 A1 | 5/2005 | Sirmans, Jr. |
| 2005/0107723 A1 | 5/2005 | Wehman et al. |
| 2005/0163056 A1 | 7/2005 | Ranta-Aho et al. |
| 2005/0171410 A1 * | 8/2005 | Hjelt ...................... A61B 5/00 600/300 |
| 2005/0228244 A1 | 10/2005 | Banet |
| 2005/0228692 A1 | 10/2005 | Hodgdon |
| 2005/0234742 A1 | 10/2005 | Hodgdon |
| 2005/0248718 A1 | 11/2005 | Howell et al. |
| 2006/0020174 A1 | 1/2006 | Matsumura et al. |
| 2006/0020177 A1 | 1/2006 | Seo et al. |
| 2006/0025282 A1 | 2/2006 | Redmann |
| 2006/0047208 A1 | 3/2006 | Yoon |
| 2006/0047447 A1 | 3/2006 | Brady et al. |
| 2006/0064276 A1 | 3/2006 | Ren et al. |
| 2006/0069619 A1 | 3/2006 | Walker et al. |
| 2006/0089542 A1 | 4/2006 | Sands |
| 2006/0111944 A1 | 5/2006 | Sirmans, Jr. |
| 2006/0129436 A1 | 6/2006 | Short |
| 2006/0143645 A1 | 6/2006 | Vock et al. |
| 2006/0217231 A1 | 9/2006 | Parks et al. |
| 2006/0247952 A1 | 11/2006 | Muraca |
| 2006/0277474 A1 | 12/2006 | Robarts et al. |
| 2006/0282021 A1 | 12/2006 | DeVaul et al. |
| 2006/0287883 A1 | 12/2006 | Turgiss et al. |
| 2007/0050715 A1 | 3/2007 | Behar |
| 2007/0051369 A1 | 3/2007 | Choi et al. |
| 2007/0071643 A1 | 3/2007 | Hall et al. |
| 2007/0072156 A1 | 3/2007 | Kaufman et al. |
| 2007/0083602 A1 | 4/2007 | Heggenhougen et al. |
| 2007/0123391 A1 | 5/2007 | Shin et al. |
| 2007/0136093 A1 | 6/2007 | Rankin et al. |
| 2007/0146116 A1 | 6/2007 | Kimbrell |
| 2007/0155277 A1 | 7/2007 | Amitai et al. |
| 2007/0159926 A1 | 7/2007 | Prstojevich et al. |
| 2007/0179356 A1 | 8/2007 | Wessel |
| 2007/0194066 A1 | 8/2007 | Ishihara et al. |
| 2007/0197920 A1 | 8/2007 | Adams |
| 2007/0208544 A1 | 9/2007 | Kulach et al. |
| 2007/0276271 A1 | 11/2007 | Chan |
| 2008/0084823 A1 | 4/2008 | Akasaka et al. |
| 2008/0093838 A1 | 4/2008 | Tropper et al. |
| 2008/0097550 A1 | 4/2008 | Dicks et al. |
| 2008/0114829 A1 | 5/2008 | Button et al. |
| 2008/0125288 A1 | 5/2008 | Case |
| 2008/0129457 A1 | 6/2008 | Ritter et al. |
| 2008/0134102 A1 | 6/2008 | Movold et al. |
| 2008/0140163 A1 | 6/2008 | Keacher et al. |
| 2008/0140338 A1 | 6/2008 | No et al. |
| 2008/0146892 A1 | 6/2008 | LeBoeuf et al. |
| 2008/0155077 A1 | 6/2008 | James |
| 2008/0176655 A1 | 7/2008 | James et al. |
| 2008/0287751 A1 | 11/2008 | Stivoric et al. |
| 2009/0018797 A1 | 1/2009 | Kasama et al. |
| 2009/0043531 A1 | 2/2009 | Kahn et al. |
| 2009/0047645 A1 | 2/2009 | Dibenedetto et al. |
| 2009/0048044 A1 | 2/2009 | Oleson et al. |
| 2009/0054737 A1 | 2/2009 | Magar et al. |
| 2009/0063193 A1 | 3/2009 | Barton et al. |
| 2009/0098821 A1 | 4/2009 | Shinya |
| 2009/0150178 A1 | 6/2009 | Sutton et al. |
| 2009/0156172 A1 | 6/2009 | Chan |
| 2009/0171788 A1 | 7/2009 | Tropper et al. |
| 2009/0184849 A1 | 7/2009 | Nasiri |
| 2009/0195350 A1 | 8/2009 | Tsern et al. |
| 2009/0262088 A1 | 10/2009 | Moll-Carrillo et al. |
| 2009/0264713 A1 | 10/2009 | Van Loenen et al. |
| 2009/0271147 A1 | 10/2009 | Sugai |
| 2009/0287921 A1 | 11/2009 | Zhu et al. |
| 2009/0307517 A1 | 12/2009 | Fehr et al. |
| 2009/0309742 A1 | 12/2009 | Alexander et al. |
| 2010/0059561 A1 | 3/2010 | Ellis et al. |
| 2010/0069203 A1 | 3/2010 | Kawaguchi et al. |
| 2010/0159709 A1 | 6/2010 | Kotani et al. |
| 2010/0167783 A1 | 7/2010 | Alameh et al. |
| 2010/0185064 A1 | 7/2010 | Bandic et al. |
| 2010/0205541 A1 | 8/2010 | Rapaport et al. |
| 2010/0217099 A1 | 8/2010 | LeBoeuf et al. |

(56) References Cited

U.S. PATENT DOCUMENTS

| | | | |
|---|---|---|---|
| 2010/0261987 A1 | 10/2010 | Kamath | |
| 2010/0331145 A1 | 12/2010 | Lakovic et al. | |
| 2011/0003665 A1* | 1/2011 | Burton | G04F 10/00 482/9 |
| 2011/0009051 A1 | 1/2011 | Khedouri et al. | |
| 2011/0022349 A1 | 1/2011 | Stirling et al. | |
| 2011/0080349 A1 | 4/2011 | Holbein et al. | |
| 2011/0087076 A1 | 4/2011 | Brynelsen et al. | |
| 2011/0106449 A1 | 5/2011 | Chowdhary et al. | |
| 2011/0131005 A1 | 6/2011 | Ueshima et al. | |
| 2011/0193704 A1 | 8/2011 | Harper et al. | |
| 2011/0197157 A1 | 8/2011 | Hoffman et al. | |
| 2011/0224508 A1 | 9/2011 | Moon | |
| 2011/0230729 A1 | 9/2011 | Shirasaki et al. | |
| 2012/0072165 A1 | 3/2012 | Jallon | |
| 2012/0083705 A1 | 4/2012 | Yuen et al. | |
| 2012/0083714 A1 | 4/2012 | Yuen et al. | |
| 2012/0083715 A1 | 4/2012 | Yuen et al. | |
| 2012/0083716 A1 | 4/2012 | Yuen et al. | |
| 2012/0084053 A1 | 4/2012 | Yuen et al. | |
| 2012/0084054 A1 | 4/2012 | Yuen et al. | |
| 2012/0092157 A1 | 4/2012 | Tran | |
| 2012/0094649 A1 | 4/2012 | Porrati et al. | |
| 2012/0119911 A1 | 5/2012 | Jeon et al. | |
| 2012/0165684 A1 | 6/2012 | Sholder | |
| 2012/0166257 A1 | 6/2012 | Shiragami et al. | |
| 2012/0183939 A1 | 7/2012 | Aragones et al. | |
| 2012/0226471 A1 | 9/2012 | Yuen et al. | |
| 2012/0226472 A1 | 9/2012 | Yuen et al. | |
| 2012/0227737 A1 | 9/2012 | Mastrototaro et al. | |
| 2012/0265480 A1 | 10/2012 | Oshima | |
| 2012/0274508 A1 | 11/2012 | Brown et al. | |
| 2012/0283855 A1 | 11/2012 | Hoffman | |
| 2012/0316456 A1 | 12/2012 | Rahman et al. | |
| 2012/0324226 A1 | 12/2012 | Bichsel et al. | |
| 2012/0330109 A1 | 12/2012 | Tran | |
| 2013/0006718 A1 | 1/2013 | Nielsen et al. | |
| 2013/0041590 A1* | 2/2013 | Burich | G06F 19/3418 702/19 |
| 2013/0072169 A1 | 3/2013 | Ross et al. | |
| 2013/0073254 A1 | 3/2013 | Yuen et al. | |
| 2013/0073255 A1 | 3/2013 | Yuen et al. | |
| 2013/0080113 A1 | 3/2013 | Yuen et al. | |
| 2013/0095459 A1 | 4/2013 | Tran | |
| 2013/0096843 A1 | 4/2013 | Yuen et al. | |
| 2013/0106684 A1 | 5/2013 | Weast et al. | |
| 2013/0151196 A1 | 6/2013 | Yuen et al. | |
| 2013/0158369 A1 | 6/2013 | Yuen et al. | |
| 2013/0166048 A1 | 6/2013 | Werner et al. | |
| 2013/0190903 A1* | 7/2013 | Balakrishnan | A61B 5/7246 700/91 |
| 2013/0191034 A1* | 7/2013 | Weast | G06F 17/00 702/19 |
| 2013/0228063 A1* | 9/2013 | Turner | G10H 1/40 84/612 |
| 2013/0231574 A1 | 9/2013 | Tran | |
| 2013/0238287 A1 | 9/2013 | Hoffman et al. | |
| 2013/0261475 A1 | 10/2013 | Mochizuki | |
| 2013/0267249 A1 | 10/2013 | Rosenberg | |
| 2013/0268199 A1 | 10/2013 | Nielsen et al. | |
| 2013/0268236 A1 | 10/2013 | Yuen et al. | |
| 2013/0268687 A1 | 10/2013 | Schrecker | |
| 2013/0274904 A1* | 10/2013 | Coza | G06F 3/011 700/91 |
| 2013/0289366 A1 | 10/2013 | Chua et al. | |
| 2013/0296666 A1 | 11/2013 | Kumar et al. | |
| 2013/0296672 A1 | 11/2013 | O'Neil et al. | |
| 2013/0296673 A1 | 11/2013 | Thaveeprungsriporn et al. | |
| 2013/0310896 A1 | 11/2013 | Mass | |
| 2013/0325396 A1 | 12/2013 | Yuen et al. | |
| 2013/0337974 A1 | 12/2013 | Yanev et al. | |
| 2014/0035761 A1 | 2/2014 | Burton et al. | |
| 2014/0039804 A1 | 2/2014 | Park et al. | |
| 2014/0039840 A1 | 2/2014 | Yuen et al. | |
| 2014/0039841 A1 | 2/2014 | Yuen et al. | |
| 2014/0052280 A1 | 2/2014 | Yuen et al. | |
| 2014/0067278 A1 | 3/2014 | Yuen et al. | |
| 2014/0077673 A1 | 3/2014 | Garg et al. | |
| 2014/0094941 A1 | 4/2014 | Ellis et al. | |
| 2014/0125618 A1* | 5/2014 | Panther | A61B 5/6838 345/173 |
| 2014/0164611 A1* | 6/2014 | Molettiere | A61B 5/6838 709/224 |
| 2014/0180022 A1 | 6/2014 | Stivoric et al. | |
| 2014/0213858 A1 | 7/2014 | Presura et al. | |
| 2014/0275885 A1 | 9/2014 | Isaacson et al. | |
| 2014/0278229 A1* | 9/2014 | Hong | A61B 5/7455 702/160 |
| 2014/0316305 A1* | 10/2014 | Venkatraman | A61B 5/1112 600/595 |
| 2015/0026647 A1 | 1/2015 | Park et al. | |

FOREIGN PATENT DOCUMENTS

| | | |
|---|---|---|
| JP | 11-347021 | 12/1999 |
| RU | 2178588 | 1/2002 |
| WO | WO 02/11019 | 2/2002 |
| WO | WO 2006/055125 | 5/2006 |
| WO | WO 2006/090197 | 8/2006 |
| WO | WO 2008/038141 | 4/2008 |
| WO | WO 2009/042965 | 4/2009 |
| WO | WO 2012/170586 | 12/2012 |
| WO | WO 2012/170924 | 12/2012 |
| WO | WO 2012/171032 | 12/2012 |
| WO | WO 2015/127067 | 8/2015 |
| WO | WO 2016/003269 | 1/2016 |

OTHER PUBLICATIONS

Fang et al., Dec. 2005, Design of a Wireless Assisted Pedestrian Dead Reckoning System—The NavMote Experience, IEEE Transactions on Instrumentation and Measurement, 54(6):2342-2358.

Godfrey et al., 2008, Direct Measurement of Human Movement by Accelerometry, Medical Engineering & Physics, 30:1364-1386.

Godha et al., May 2008, Foot Mounted Inertia System for Pedestrian Navigation, Measurement Science and Technology, 19(7):1-9.

Intersema App., Using MS5534 for altimeters and barometers, Note AN501, Jan. 2006.

Ladetto et al., Sep. 2000, On Foot Navigation: When GPS alone is not Enough, Journal of Navigation, 53(2):279-285.

Lammel et al., Sep. 2009, Indoor Navigation with MEMS Sensors, Proceedings of the Eurosensors XIII conference, 1(1):532-535.

Lester et al., 2005, A Hybrid Discriminative/Generative Approach for Modeling Human Activities, Proc. of the Int'l Joint Conf. Artificial Intelligence, pp. 766-772.

Lester et al., 2009, Validated caloric expenditure estimation using a single body-worn sensor, Proc. of the Int'l Conf. on Ubiquitous Computing, pp. 225-234.

Ohtaki et al., Aug. 2005, Automatic classification of ambulatory movements and evaluation of energy consumptions utilizing accelerometers and barometer, Microsystem Technologies, 11(8-10:)1034-1040.

Parkka et al., Jan. 2006, Activity Classification Using Realistic Data From Wearable Sensors, IEEE Transactions on Information Technology in Biomedicine, 10(1):119-128.

Perrin et al., 2000, Improvement of Walking Speed Prediction by Accelerometry and Altimetry, Validated by Satellite Positioning, Medical & Biological Engineering & Computing, 38:164-168.

Retscher, 2006, An Intelligent Multi-Sensor system for Pedestrian Navigation, Journal of Global Positioning Systems, 5(1):110-118.

Sagawa et al., Aug.-Sep. 1998, Classification of Human Moving Patterns Using Air Pressure and Acceleration, Proceedings of the 24.sup.th Annual Conference of the IEEE Industrial Electronics Society, 2:1214-1219.

Sagawa et al., Oct. 2000, Non-restricted measurement of walking distance, IEEE Int'l Conf. on Systems, Man, and Cybernetics, 3:1847-1852.

(56) References Cited

OTHER PUBLICATIONS

SCP 1000-D01/D11 Pressure Sensor as Barometer and Altimeter, VTI Technologies Application, Jun. 2006, Note 33.
Stirling et al., 2005, Evaluation of a New Method of Heading Estimation of Pedestrian Dead Reckoning Using Shoe Mounted Sensors, Journal of Navigation, 58:31-45.
Suunto LUMI User Guide, Jun. and Sep. 1997.
Tanigawa et al., Mar. 2008, Drift-free dynamic height sensor using MEMS IMU aided by MEMS pressure sensor, Workshop on Positioning, Navigation and Communication, pp. 191-196.
International Search Report issued on Aug. 15, 2008, in related application PCT/IB07/03617.
Specification of the Bluetooth® System, Core Package, version 4.1, Dec. 2013, vols. 0 & 1, 282 pages.

\* cited by examiner

USER MESSAGING BASED ON CHANGES IN TRACKED ACTIVITY METRICS

CLAIM OF PRIORITY

This application claims priority as a continuation of U.S. application Ser. No. 14/445,033, filed Jul. 28, 2014, entitled "Fitness Activity Related Messaging," which claims priority as a continuation-in-part of U.S. application Ser. No. 14/271,412, filed May 6, 2014 (now issued as U.S. Pat. No. 9,031,812), entitled "Notifications on a User Device Based on Activity Detected by an Activity Monitoring Device." The disclosures of these applications are herein incorporated by reference in their entirety for all purposes.

RELATED APPLICATIONS

This application is related to U.S. application Ser. No. 14/445,034, filed Jul. 28, 2014, entitled "Notifications Regarding Interesting or Unusual Activity Detected from an Activity Monitoring Device," the disclosure of which is herein incorporated by reference in its entirety for all purposes.

FIELD

The present disclosure relates to systems and methods for fitness activity related messaging.

BACKGROUND

In recent years, the need for health and fitness has grown tremendously. The growth has occurred due to a better understanding of the benefits of good fitness to overall health and wellness. Unfortunately, although today's modern culture has brought about many new technologies, such as the Internet, connected devices and computers, people have become less active. Additionally, many office jobs require people to sit in front of computer screens for long periods of time, which further reduces a person's activity levels. Furthermore, much of today's entertainment options involve viewing multimedia content, computer social networking, and other types of computer involved interfacing. Although such computer activity can be very productive as well as entertaining, such activity tends to reduce a person's overall physical activity.

To provide users concerned with health and fitness a way of measuring or accounting for their activity or lack thereof, fitness activity trackers have recently grown in popularity. Fitness activity trackers are used to measure activity, such as walking, motion, running, sleeping, being inactive, bicycling, exercising on an elliptical trainer, and the like. Typically, the data collected by such devices can be transferred and viewed on a computing device.

It is in this context that embodiments of the invention arise.

SUMMARY

Embodiments described in the present disclosure provide systems, apparatus, computer readable media, and methods for fitness activity related messaging.

In one embodiment, a method for generating a message to a friend of a user is provided, comprising: processing activity data of a first user measured by an activity monitoring device to update a value of an activity metric for the first user; identifying a change in an inequality relationship between the value of the activity metric for the first user and a value of the activity metric for a second user; in response to identifying the change in the inequality relationship, prompting the first user to generate a message to the second user.

In one embodiment, the change in the inequality relationship is defined by the value of the activity metric for the first user changing, from being less than the value of the activity metric for the second user, to being greater than the value of the activity metric for the second user.

In one embodiment, the change in the inequality relationship is defined by the value of the activity metric for the first user changing, from being greater than the value of the activity metric for the second user, to being less than the value of the activity metric for the second user.

In one embodiment, the inequality relationship between the value of the activity metric for the first user and the value of the activity metric for the second user defines a relative ranking of the first user and the second user on a competitive leaderboard for the activity metric.

In one embodiment, the change in the inequality relationship defines a change in the relative ranking of the first user and the second user on the competitive leaderboard for the activity metric.

In one embodiment, prompting the user to generate a message includes identifying the change in the relative ranking of the first user and the second user.

In one embodiment, prompting the first user to generate a message to the second user includes triggering a notification to the first user, the notification providing access to an interface configured to receive input from the first user to define content of the message to the second user.

In one embodiment, the notification is a push notification to a mobile device.

In one embodiment, the interface provides at least one option to send a predefined message to the second user.

In one embodiment, the activity metric is defined by one or more of the following: stepcount, elevation climbed, distance traveled, active amount of time.

In another embodiment, a method for providing a competitive leaderboard is provided, comprising: receiving a request to display a messaging thread, the messaging thread defined by one or more messages between members of the messaging thread; in response to the request, presenting the messaging thread; for each of the members, retrieving a value of an activity metric; determining a ranked order for the members based on each member's respective value of the activity metric; presenting a leaderboard in conjunction with the messaging thread, the leaderboard defined to display each member's value of the activity metric according to the ranked order; wherein the method is executed by at least one processor.

In one embodiment, the value for the activity metric for a given member is processed from activity data captured by an activity monitoring device associated with the given member.

In one embodiment, receiving the request to display the messaging thread is defined by access activity associated with an inbox defined for a member of the messaging thread.

In one embodiment, the method further comprises: determining whether each of the members of the messaging thread are linked to each other on a social network, and if so, then performing the operation of presenting the leaderboard, and if not, then not performing the operation of presenting the leaderboard.

In one embodiment, the activity metric is selected from a quantity of steps taken, a quantity of floors climbed, or a quantity of calories burned.

In another embodiment, a method for generating a competitive group is provided, comprising: determining a number of messages in a message thread; when the number of messages in the message thread reaches a predefined threshold, providing an option to a first member of the message thread to generate a competitive group for members of the message thread; in response to activation of the option by the first member, sending invitations to remaining members of the message thread to join the competitive group; receiving responses to the sent invitations; generating the competitive group, the competitive group defined to include the first member and, each of the remaining members of the message thread that provides a positive response to the invitation; wherein membership in the competitive group provides access to a value of an activity metric for each of the members of the competitive group.

In one embodiment, the value for the activity metric for a member of the competitive group is processed from activity data captured by an activity monitoring device associated with the member.

In one embodiment, activation of the option includes identifying the activity metric for which membership in the competitive group provides access.

In one embodiment, the activity metric is selected from a quantity of steps taken, a quantity of floors climbed, or a quantity of calories burned.

In another embodiment, a method for forming a competitive group is provided, comprising: determining a quantity of messaging from a first user to one or more second users; when the quantity of messaging exceeds a predefined threshold, then providing an option to the first user to create a competitive group inclusive of the first user and the one or more second users; wherein membership in the competitive group provides access to values of an activity metric for each of the members of the competitive group.

In one embodiment, the quantity of messaging is defined by a number of messages sent from the first user to the one or more second users.

In one embodiment, the quantity of messaging is defined by a frequency of messages sent from the first user to the one or more second users.

In one embodiment, the method further comprises: in response to activation of the option to create the competitive group, sending invitations to each of the one or more second users to join the competitive group; receiving responses to the invitations; generating the competitive group based on the responses to the invitations.

In one embodiment, membership in the competitive group provides access to a group leaderboard, the group leaderboard configured to present a ranked order of the members of the group according to the values of the activity metric for each of the members of the competitive group. In another embodiment, a method is provided, comprising: receiving activity data associated with a first user account, the activity data associated with the first user account being determined from motion data detected by an activity tracking device associated with the first user account; receiving activity data associated with a second user account, the activity data associated with the second user account being determined from motion data detected by an activity tracking device associated with the second user account; processing the activity data associated with the first user account to determine a cumulative activity level for the first user account; processing the activity data associated with the second user account to determine a cumulative activity level for the second user account; comparing the cumulative activity levels for the first and second user accounts; in response to detecting a passing event, defined by the cumulative activity level of the first or second user account surpassing that of the other, then generating and sending a message to the first user account and/or the second user account, the message identifying the passing event.

In one embodiment, generating the message includes selecting a message template for the passing event, and populating the message template with customized data based on the activity metrics of the first and/or second user account.

In one embodiment, selecting the message template is based on a magnitude of a difference between the cumulative activity levels of the first and second user accounts.

In one embodiment, selecting the message template is based on whether the message is to be sent to the first user account or the second user account.

In one embodiment, the activity metrics include one or more of steps taken, stairs climbed, floors climbed, distance traveled, active minutes, heart rate, and/or sleep data.

In one embodiment, sending the message to the first or second user account effects display of the message on one or more of the activity tracking device or a mobile device that is associated to the first or second user account, respectively.

In one embodiment, sending the message is defined by one or more of a push notification, a private message, or an e-mail.

In one embodiment, the method further includes: generating and sending a message identifying the passing event to a third user account, the third user account being identified as a member of a social graph of the first or second user account.

Other aspects will become apparent from the following detailed description, taken in conjunction with the accompanying drawings, illustrating by way of example the principles of embodiments described in the present disclosure.

BRIEF DESCRIPTION OF THE DRAWINGS

Various embodiments described in the present disclosure may best be understood by reference to the following description taken in conjunction with the accompanying drawings.

DETAILED DESCRIPTION

Figure 1A:
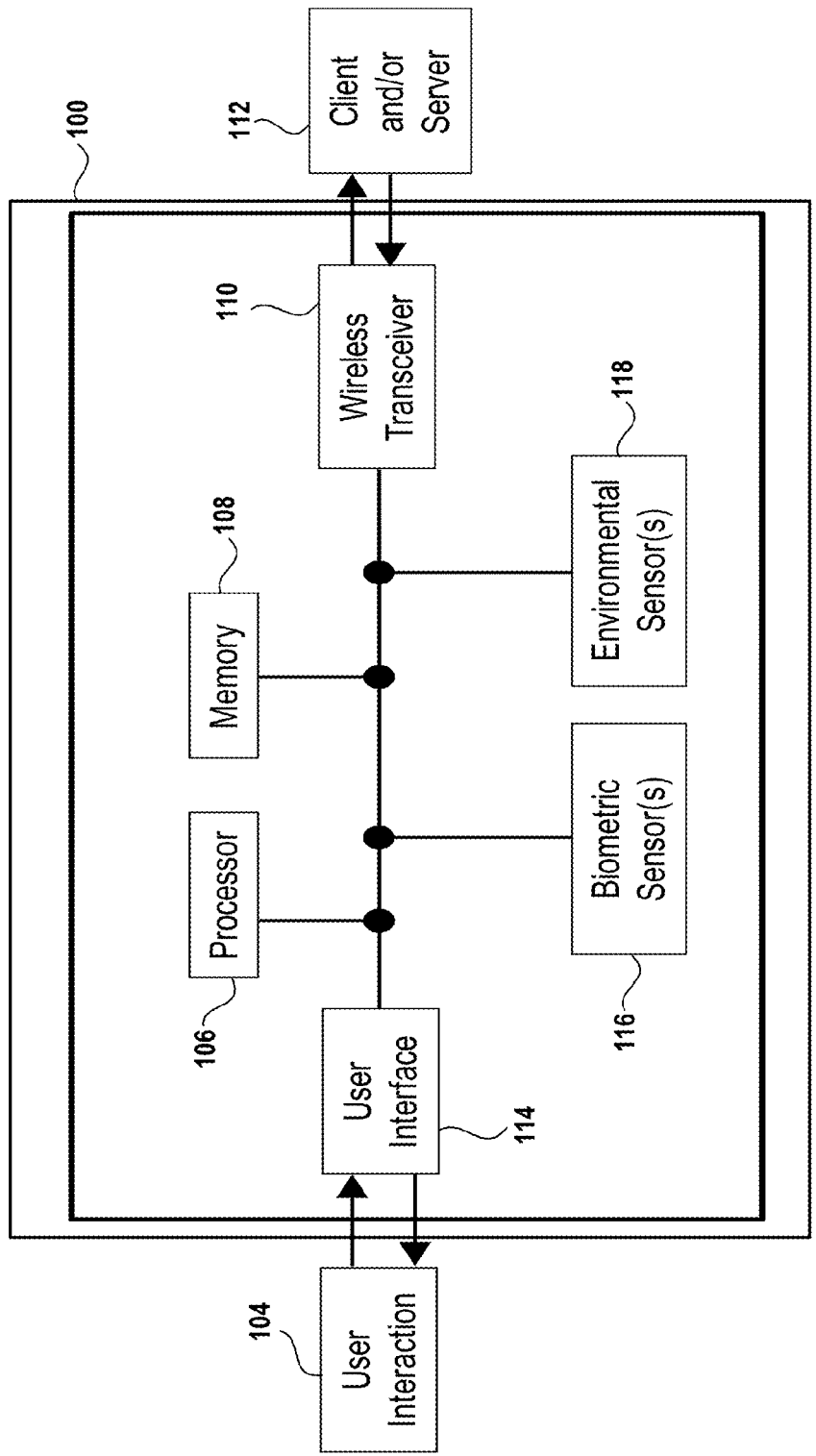
FIG. 1A shows a block diagram of an activity tracking device, in accordance with one embodiment of the present invention.

Embodiments described in the present disclosure provide systems, apparatus, computer readable media, and methods for fitness activity related messaging.

It should be noted that there are many inventions described and illustrated herein. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

Further, in the course of describing and illustrating the present inventions, various circuitry, architectures, structures, components, functions and/or elements, as well as combinations and/or permutations thereof, are set forth. It should be understood that circuitry, architectures, structures, components, functions and/or elements other than those specifically described and illustrated, are contemplated and are within the scope of the present inventions, as well as combinations and/or permutations thereof.

FIG. 1 shows a block diagram of an activity tracking device 100, in accordance with one embodiment of the present invention. The activity tracking device 100 is contained in a housing, which may be worn or held by a user. The housing may be in the form of a wristband, a clip on device, a wearable device, or may be held by the user either in the user's hand or in a pocket or attached to the user's body. The activity tracking device 100 includes device components 102, which may be in the form of logic, storage, and glue logic, one or more processors, microelectronics, and interfacing circuitry. In one example, the components 102 will include a processor 106, memory 108, a wireless transceiver 110, a user interface 114, biometric sensors 116, and environmental sensors 118.

The environmental sensors 118 may be in the form of motion detecting sensors. In some embodiments, a motion sensor can be one or more of an accelerometer, or a gyroscope, or a rotary encoder, or a calorie measurement sensor, or a heat measurement sensor, or a moisture measurement sensor, or a displacement sensor, or an ultrasonic sensor, or a pedometer, or an altimeter, or a linear motion sensor, or an angular motion sensor, or a multi-axis motion sensor, or a combination thereof. The biometric sensors 116 can be defined to measure physiological characteristics of the user that is using the activity tracking device 100. The user interface 114 provides a way for communicating with the activity tracking device 100, in response to user interaction 104. The user interaction 104 can be in the form of physical contact (e.g., without limitation, tapping, sliding, rubbing, multiple taps, gestures, etc.).

In some embodiments, the user interface 114 is configured to receive user interaction 104 by way of proximity sensors, button presses, touch sensitive screen inputs, graphical user interface inputs, voice inputs, sound inputs, etc. The activity tracking device 100 can communicate with a client and/or server 112 using the wireless transceiver 110. The wireless transceiver 110 will allow the activity tracking device 100 to communicate using a wireless connection, which is enabled by wireless communication logic. The wireless communication logic can be in the form of a circuit having radio communication capabilities. The radio communication capabilities can be in the form of a Wi-Fi connection, a Bluetooth connection, a low-energy Bluetooth connection, or any other form of wireless tethering or near field communication. In still other embodiments, the activity tracking device 100 can communicate with other computing devices using a wired connection (not shown). As mentioned, the environmental sensors 118 can detect motion of the activity tracking device 100.

The motion can be activity of the user, such as walking, running, stair climbing, etc. The motion can also be in the form of physical contact received on any surface of the activity tracking device 110, so long as the environmental sensors 118 can detect such motion from the physical contact. Such physical contact may be in the form of a tap or multiple taps by a finger upon the housing of the activity tracking device 100.

Figure 1B:
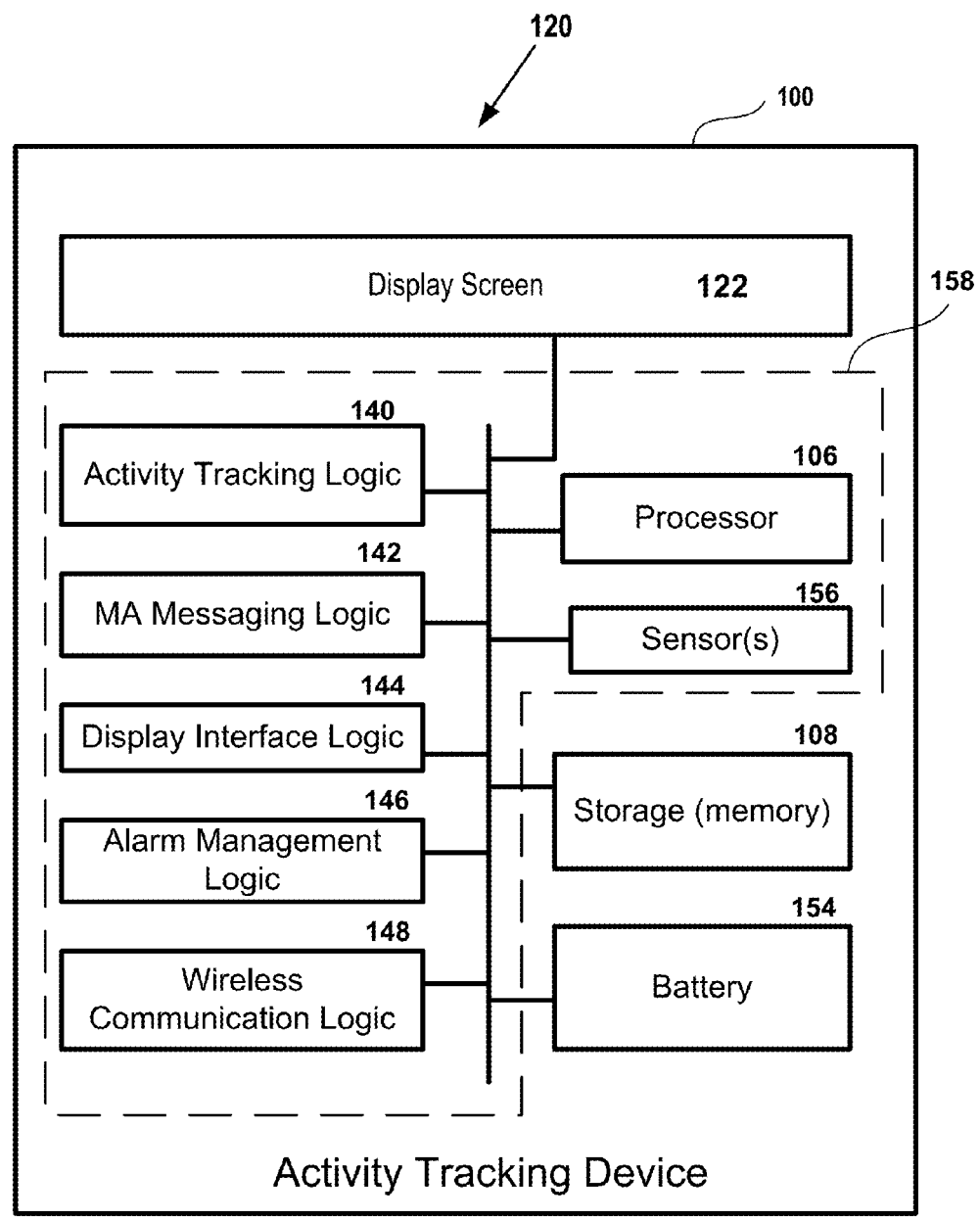
FIG. 1B illustrates an example of an activity tracking device including example components utilized for tracking activity and motion of the device, and associated interfaces to a display screen, in accordance with one embodiment of the present invention.

FIG. 1B illustrates an example of activity tracking device 100 of FIG. 1A, showing some additional example components utilized for tracking activity and motion of the device, and associated interfaces to display screen 122. In one embodiment, examples of a display screen 122 can include, but are not limited to, liquid crystal display (LCD) screens, light emitting diode (LED) screens, organic light emitting diode (OLED) screens, plasma display screens, etc.

As shown in FIG. 1B, the activity tracking device 100 includes logic 158. Logic 158 may include activity tracking logic 140, motion-activated messaging logic 142, display interface logic 144, alarm management logic 146, wireless communication logic 148, processor 106, and sensors 156. Additionally, storage (e.g. memory) 108, and a battery 154 can be integrated within the activity tracking device 100. The activity tracking logic 140 can include logic that is configured to process motion data produced by sensors 156, so as to quantify the motion and produce identifiable metrics associated with the motion.

Some motions will produce and quantify various types of metrics, such as step count, stairs climbed, distance traveled, very active minutes, calories burned, etc. The physical contact logic 142 can include logic that calculates or determines when particular physical contact can qualify as an input. To qualify as an input, the physical contact detected by sensors 156 should have a particular pattern that is identifiable as input. For example, the input may be pre-defined to be a double tap input, and the physical contact logic 142 can analyze the motion to determine if a double tap indeed occurred in response to analyzing the sensor data produced by sensors 156.

The display interface logic 144 is configured to interface with the processor and the motion-activated messaging logic to determine when specific messages will be displayed on the display screen 122 of the activity tracking device 100. The display interface logic 144 can act to turn on the screen, display metric information, display characters or alphanumeric information, display graphical user interface graphics, or combinations thereof. Alarm management logic 146 can function to provide a user interface and settings for managing and receiving input from a user to set an alarm. The alarm management logic can interface with a timekeeping module (e.g., clock, calendar, time zone, etc.), and can trigger the activation of an alarm. The alarm can be in the form of an audible alarm or a non-audible alarm.

A non-audible alarm can provide such alarm by way of a vibration. The vibration can be produced by a motor integrated in the activity tracking device 100. The vibration can be defined to include various vibration patterns, intensities, and custom set patterns. The vibration produced by the motor or motors of the activity tracking device 100 can be managed by the alarm management logic 146 in conjunction with processing by the processor 106. The wireless communication logic 148 is configured for communication of the activity tracking device with another computing device by way of a wireless signal. The wireless signal can be in the form of a radio signal. As noted above, the radio signal can be in the form of a Wi-Fi signal, a Bluetooth signal, a low energy Bluetooth signal, or combinations thereof. The wireless communication logic can interface with the processor 106, storage 108 and battery 154 of device 100, for transferring activity data, which may be in the form of motion data or processed motion data, stored in the storage 108 to the computing device.

In one embodiment, processor 106 functions in conjunction with the various logic components 140, 142, 144, 146, and 148. The processor 106 can, in one embodiment, provide the functionality of any one or all of the logic components. In other embodiments, multiple chips can be used to separate the processing performed by any one of the logic components and the processor 106. Sensors 156 can communicate via a bus with the processor 106 and/or the logic components. The storage 108 is also in communication with the bus for providing storage of the motion data processed or tracked by the activity tracking device 100. Battery 154 is provided for providing power to the activity tracking device 100.

Figure 2:
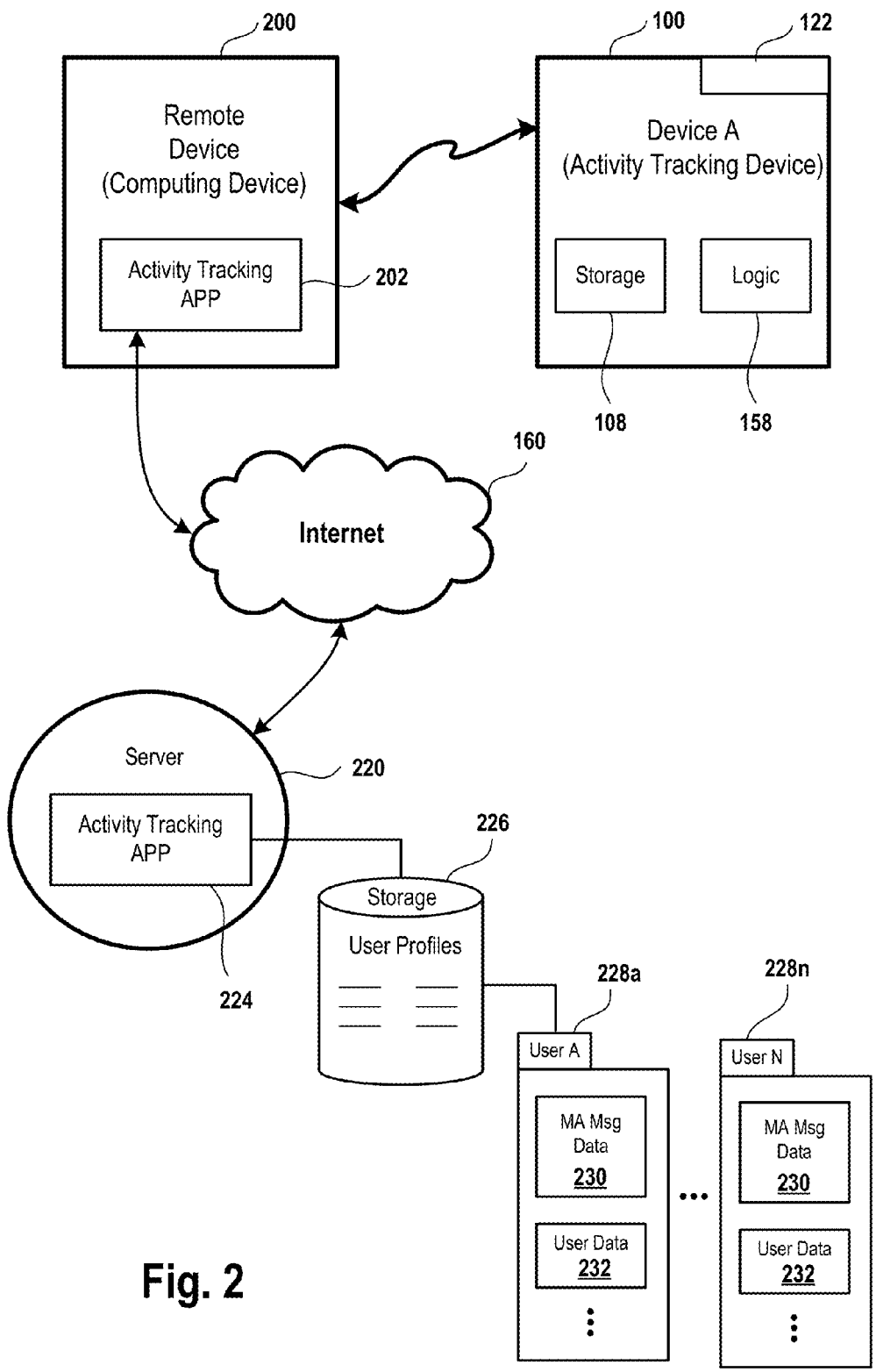
FIG. 2 illustrates an example of activity tracking device in communication with a remote device, in accordance with one embodiment of the present invention.

FIG. 2 illustrates an example of activity tracking device 100 in communication with a remote device 200. Remote device 200 is a computing device that is capable of communicating wirelessly with activity tracking device 100 and with the Internet 160. Remote device 200 can support installation and execution of applications. Such applications can include an activity tracking application 202. Activity tracking application 202 can be downloaded from a server. The server can be a specialized server or a server that provides applications to devices, such as an application store. Once the activity tracking application 202 is installed in the remote device 200, the remote device 200 can communicate or be set to communicate with activity tracking device 100 (Device A). The remote device 200 can be a smartphone, a handheld computer, a tablet computer, a laptop computer, a desktop computer, or any other computing device capable of wirelessly interfacing with Device A and the Internet.

In one embodiment, remote device 200 communicates with activity tracking device 100 over a Bluetooth connection. In one embodiment, the Bluetooth connection is a low energy Bluetooth connection (e.g., Bluetooth LE, BLE, or Bluetooth Smart). Low energy Bluetooth is configured for providing low power consumption relative to standard Bluetooth circuitry. Low energy Bluetooth uses, in one embodiment, a 2.4 GHz radio frequency, which allows for dual mode devices to share a single radio antenna. In one embodiment, low energy Bluetooth connections can function at distances up to 50 meters, with over the air data rates ranging between 1-3 megabits (Mb) per second. In one embodiment, a proximity distance for communication can be defined by the particular wireless link, and is not tied to any specific standard. It should be understood that the proximity distance limitation will change in accordance with changes to existing standards and in view of future standards and/or circuitry and capabilities.

Remote device 200 can also communicate with the Internet 160 using an Internet connection. The Internet connection of the remote device 200 can include cellular connections, wireless connections such as Wi-Fi, and combinations thereof (such as connections to switches between different types of connection links). The remote device, as mentioned above, can be a smartphone or tablet computer, or any other type of computing device having access to the Internet and with capabilities for communicating with the activity tracking device 100.

A server 220 is also provided, which is interfaced with the Internet 160. The server 220 can include a number of applications that service the activity tracking device 100, and the associated users of the activity tracking device 100 by way of user accounts. For example, the server 220 can include an activity management application 224. The activity management application 224 can include logic for providing access to various devices 100, which are associated with user accounts managed by server 220. Server 220 can include storage 226 that includes various user profiles associated with the various user accounts. The user account 228a for user A and the user account 228n for user N are shown to include various information.

The information can include, without limitation, data associated with motion-activated messaging 230, user data, etc. The motion-activated messaging data 230 includes information regarding a user's preferences, settings, and configurations which are settable by the user or set by default at the server 220 when accessing a respective user account. The storage 226 will include any number of user profiles, depending on the number of registered users having user accounts for their respective activity tracking devices. It should also be noted that a single user account can have various or multiple devices associated therewith, and the multiple devices can be individually customized, managed and accessed by a user. In one embodiment, the server 220 provides access to a user to view the user data 232 associated with activity tracking device.

The data viewable by the user includes the tracked motion data, which is processed to identify a plurality of metrics associated with the motion data. The metrics are shown in various graphical user interfaces of a website enabled by the server 220. The website can include various pages with graphical user interfaces for rendering and displaying the various metrics for view by the user associated with the user account. In one embodiment, the website can also include interfaces that allow for data entry and configuration by the user.

The monitoring device of the present inventions may use one, some or all of the following sensors to acquire physiological data, including the physiological data outlined in the table below. All combinations and permutations of physiological sensors and/or physiological data are intended to fall within the scope of the present inventions. The monitoring device of the present inventions may include but is not limited to the types one, some or all of sensors specified below to acquire the corresponding physiological data; indeed, other type(s) of sensors may be employed to acquire the corresponding physiological data, which are intended to fall within the scope of the present inventions. Additionally, the device may derive the physiological data from the corresponding sensor output data, but is not limited to the number or types of physiological data that it could derive from said sensor.

TABLE

| Physiological Sensors | Physiological data acquired |
| --- | --- |
| Optical Reflectometer | Heart Rate, Heart Rate Variability |
| Potential embodiments: | SpO2 (Saturation of Peripheral Oxygen) |
| Light emitter and receiver | Respiration |
| Multi or single LED and photo diode arrangement | Stress |
| | Blood pressure |
| Wavelength tuned for specific physiological signals | Arterial Stiffness |
| | Blood glucose levels |
| Synchronous detection/amplitude modulation | Blood volume |
| | Heart rate recovery |
| | Cardiac health |
| Motion Detector | Activity level detection |
| Potential embodiments: | Sitting/standing detection |
| Inertial, Gyro or Accelerometer | Fall detection |
| GPS | |
| Skin Temp | Stress |
| EMG | Muscle tension |
| EKG | Heart Rate, Heart Rate Variability, |
| Potential Embodiments: | Heart Rate Recovery |
| 1 lead | Stress |

TABLE-continued

| Physiological Sensors | Physiological data acquired |
| --- | --- |
| 2 lead | Cardiac health |
| Magnetometer | Activity level based on rotation |
| Laser Doppler | |
| Power Meter | |
| Ultra Sound | Blood flow |
| Audio | Heart Rate, Heart Rate Variability, |
| | Heart Rate Recovery |
| | Laugh detection |
| | Respiration |
| | Respiration type-snoring, breathing, breathing problems |
| | User's voice |
| Strain gauge | Heart Rate, Heart Rate Variability |
| Potential embodiment: | Stress |
| In a wrist band | |
| Wet sensor | Stress |
| Potential embodiment: | Swimming detection |
| galvanic skin response | Shower detection |

Additional examples of types of data which may be acquired by, or processed from data acquired by, a monitoring device in accordance with embodiments of the invention, are further described in U.S. application Ser. No. 14/221,234, filed Mar. 20, 2014, entitled "Portable Monitoring Devices for Processing Applications and Processing Analysis of Physiological Conditions of a User Associated With the Portable Monitoring Device," the disclosure of which is herein incorporated by reference for all purposes.

Figure 3:
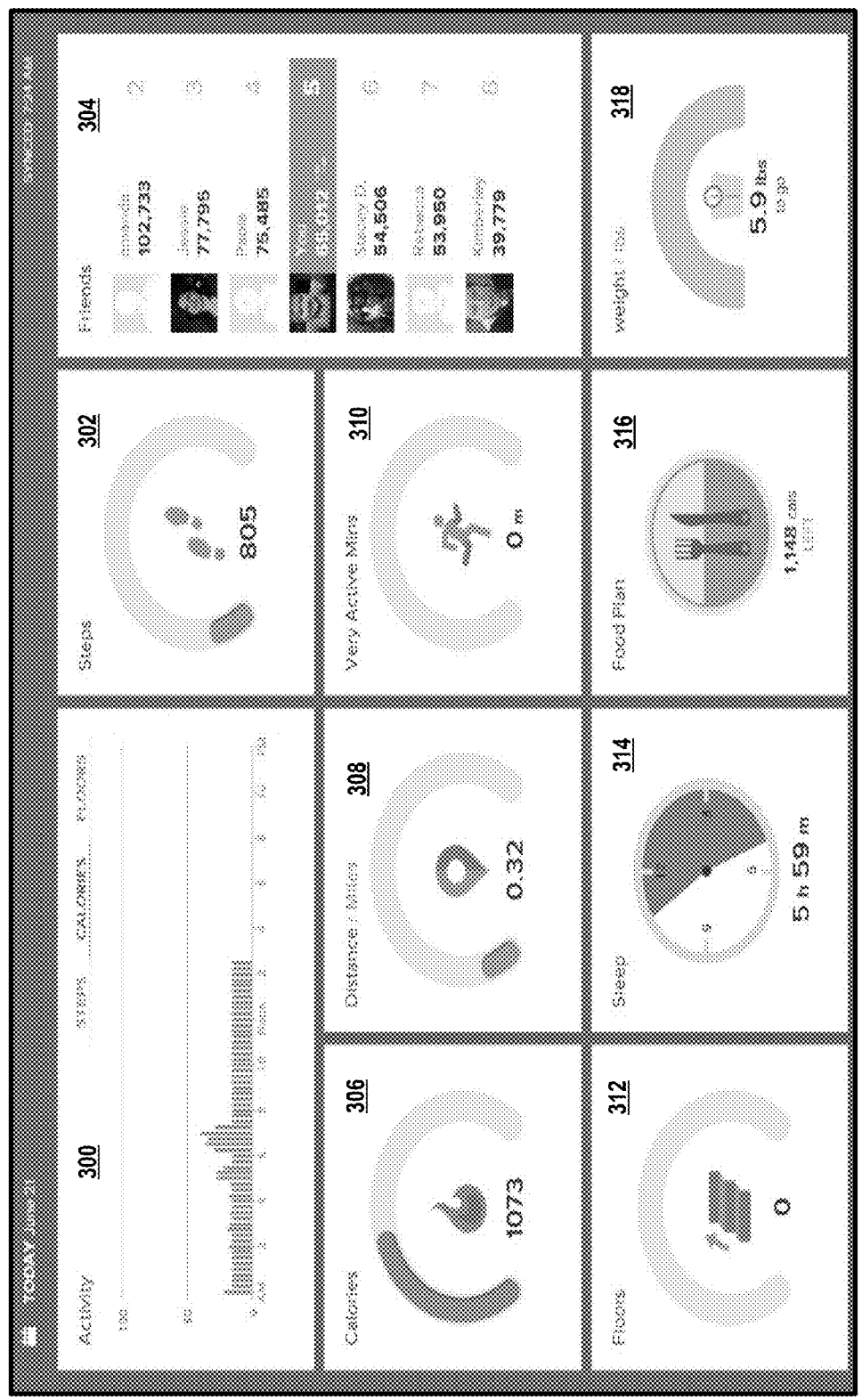
FIG. 3 illustrates an interface configured to display activity metrics/data based on activity data recorded by an activity tracking device, in accordance with an embodiment of the invention.

FIG. 3 illustrates an interface configured to display activity metrics/data based on activity data recorded by an activity tracking device, in accordance with an embodiment of the invention. It will be appreciated that the illustrated interface is provided by way of example only, without limitation, for purposes of illustrating possible elements of an interface which may be utilized by a user to understand their personal activity metrics as well as those of friends. Broadly speaking, the illustrated interface is organized into various information modules or panels which are configured to display various types of information.

A recent activity module 300 is configured to graphically display various metrics from recently detected activity of the user, such as the number of calories burned over time, a number of steps taken over time, or a number of floors climbed over time. In the illustrated embodiment, the module 300 is configured to display a number of calories burned during the course of the present day. A steps module 302 is configured to display a total number of steps taken over a given time period (e.g. last hour, current day, current week, etc.) or towards a particular goal or milestone. In one embodiment, the display of the step count is graphically portrayed, e.g. by a circular meter.

A friends module 304 is configured to display a listing of friends of the user on a social network. The friends are members of a social graph of the user that is defined by the social network. In the illustrated embodiment, the listing of friends includes names (or user names) of the friends of the user along with their profile pictures, and also includes a value of an activity metric for each of the friends. In the illustrated embodiment, each friend listed also includes a step count for that friend. In one embodiment, the friends are listed according to the activity metric, e.g. in descending order from highest to lowest total step count. In this manner, the friends module 304 provides a ranked ordering of the friends of the user, and may also show where the user ranks amongst his/her friends with respect to the particular activity metric. As discussed in further detail below, the user may initiate messaging to a friend, e.g. by clicking on or otherwise selecting the friend's entry in the friends module 304.

A calories module 306 is configured to display a number of calories burned by the user over a given period of time, e.g. during the current day. In one embodiment, a graphical representation of the number of calories burned may be provided, such as a meter or graph.

A distance module 308 is configured to display a distance traveled by the user over a given time period, e.g. during the current day. The distance traveled can also be graphically represented by a meter or graph.

An active minutes module 310 is configured to display a number of minutes for which the user has been engaged in increased levels of activity, during a given time period, e.g. during the current day. The number of active minutes can be graphically represented by a meter or graph.

A sleep module 314 is configured to display an amount of time that the user has spent sleeping, e.g. during a recent time period such as the previous 24-hour period, or the most recent period of sleep. In one embodiment, the amount of sleep can be graphically represented by an identified portion of a clock.

A food plan module 316 is configured to display information related to the user's diet or food plan. In one embodiment, the food plan module 316 is configured to display a number of calories remaining for consumption by the user during that day before exceeding a target number of calories. In one embodiment, the number of calories remaining can be represented graphically by a meter.

A weight module 318 is configured to information related to the weight of the user, such as the current weight of the user or an amount of weight remaining to lose in order to reach a target weight. In one embodiment, the weight information can be graphically represented by a meter or graph.

Figure 4:
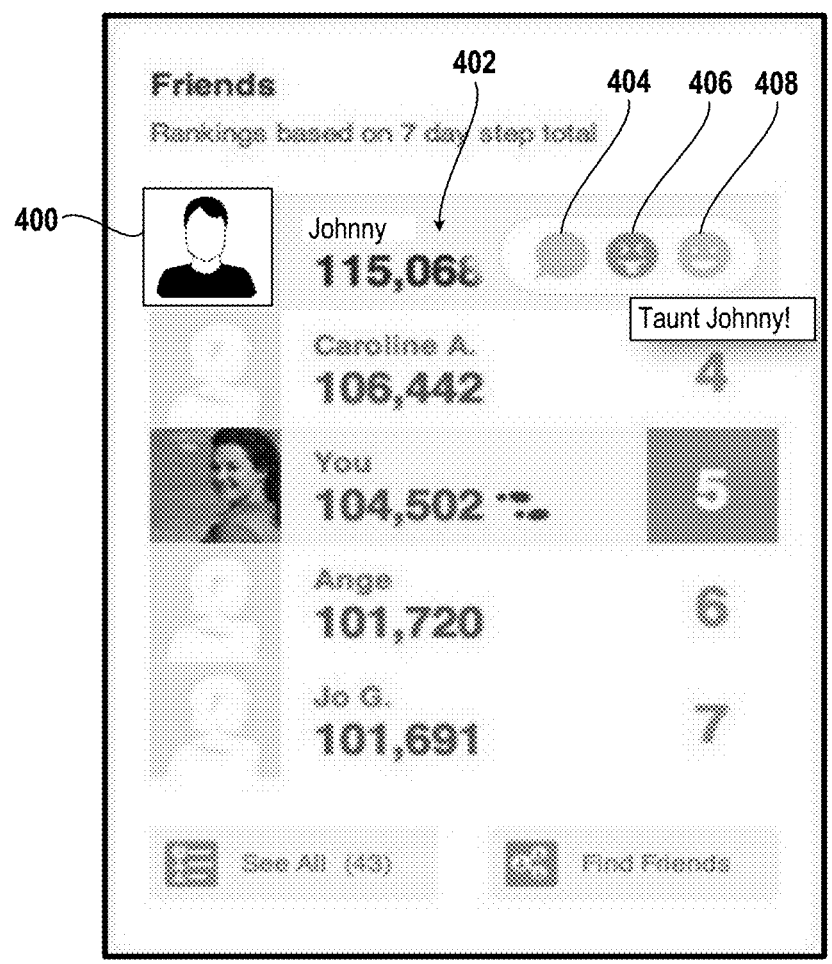
FIG. 4 illustrates a listing of members from a social graph of a user, in accordance with an embodiment of the invention.

FIG. 4 illustrates a listing of members from a social graph of a user, in accordance with an embodiment of the invention. The social graph is defined on a social network of users, each of whom has an account on the social network. Each user's account is configured to track activity data and metrics associated with that user, including that which is based on data recorded by an activity tracking device associated with the user. In this manner, the social network differs from other types of social networks in that activity data and metrics of various users can be made available to members of the social graph of a user, and even to members of the social network in general if the user so chooses based on user settings.

Thus, in the illustrated embodiment, the listing of each member of the social graph of the user additionally includes a value for an activity metric that is associated with that particular member. In the illustrated embodiment, a seven-day total step count is provided. Furthermore each of the listed members of the social graph is ranked according to their seven-day total step count, and the members of the social graph are listed in order according to their determined ranking. In this manner, the listing of members from the social graph of the user also functions as a leaderboard, displaying a ranked ordering of users based on values for an activity metric for each of the users.

Though in the illustrated embodiment, a seven-day step total is utilized, it will be appreciated that in other embodiments, any activity metric can be displayed and/or utilized for purposes of determining a ranking of members of the social graph of the user, wherein the ranking is applied to determine the order of a listing of members of the social graph of the user. In some embodiments, the ranking may be determined by a combination of activity metrics, or with reference to individualized goals.

With continued reference to FIG. 4, the listing for the user "Johnny" is defined to include a profile picture 400, and Johnny's seven-day step total (ref. 402, 115,068 steps). The listing/leaderboard of members of the social graph of the user additionally serves as a launch point for generating a message to another user. Broadly speaking, each user is associated with an account that is defined to be capable of sending and receiving messages to other users. In the illustrated embodiment, when the current user selects the listing for the user Johnny (e.g. by hovering a mouse pointer over, clicking on, or otherwise indicating selection of, Johnny's listing entry), then several options for messaging are presented to the user.

In the illustrated embodiment, an icon 404 may be selected to initiate generation of a normal message to the user Johnny. An icon 406 may be selected to initiate generation of a taunting message to the user Johnny. And an icon 408 can be selected to initiate generation of a cheering message to the user Johnny Selection of any of the foregoing icons may trigger display of a text entry field for the user to enter text to define the message. In one embodiment, sending of a normal message requires entry of text, whereas sending of a taunting message or a cheering message does not require entry of text.

Figure 5B:
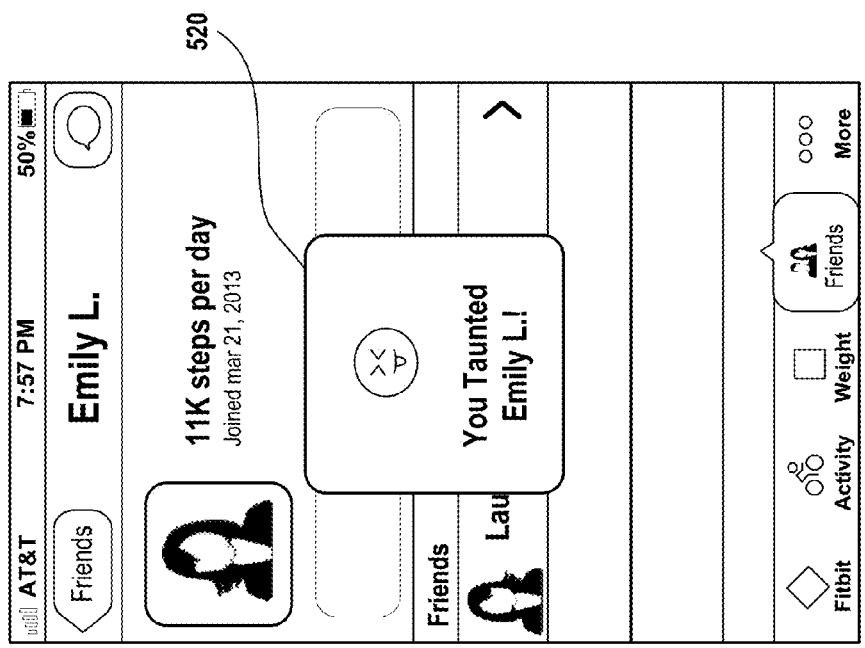
FIG. 5B illustrates a confirmation of a sent message to another user of a social network, in accordance with an embodiment of the invention.
Figure 5A:
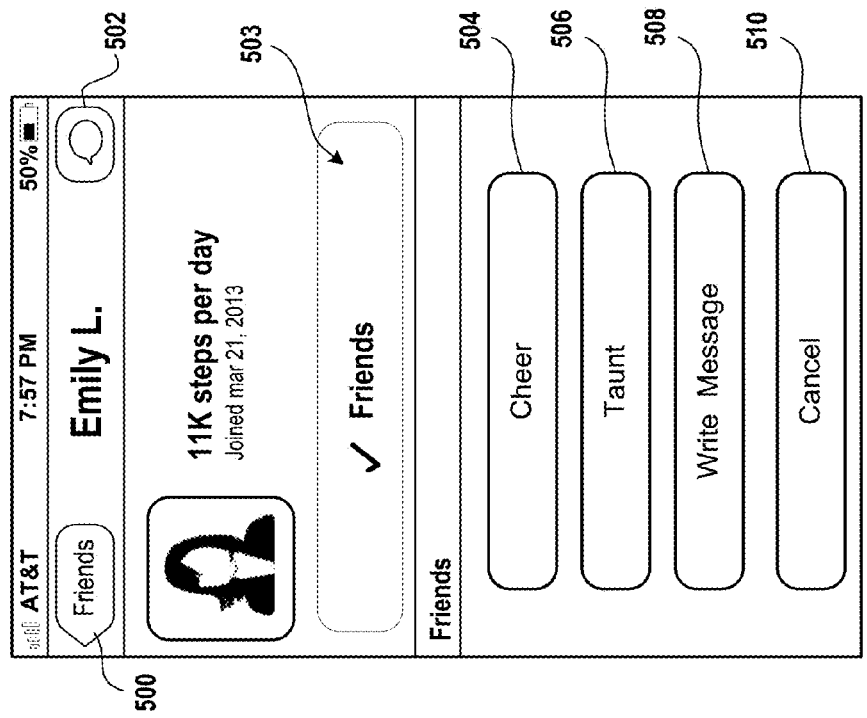
FIG. 5A illustrates an interface for selected a type of message to send to a user on a social network, in accordance with an embodiment of the invention.

FIG. 5A illustrates an interface for selected a type of message to send to a user on a social network, in accordance with an embodiment of the invention. In one embodiment, the interface shown can be configured to display on a mobile device, whereas in other embodiments, the interface can be configured display on any device capable of supporting the functionality described herein for selecting a type of message.

In one embodiment, the interface may have been reached by navigating from a listing of friends of the current user on the social network, e.g. by selecting a particular friend from the listing in order to view additional details about the selected friend. In the illustrated embodiment, details about a friend of the current user named "Emily" are displayed, including the number of steps taken by Emily per day as well as the date Emily joined the social network. A button 500 is provided for navigating back to the listing of friends. A button 502 is provided for initiating a procedure for generating a message to Emily, which as shown, has resulted in the display of a message type selection interface 503 for determining a type of message to generate to the user Emily.

A button 504 is provided for generating a cheering message. When selected the button 504 is selected, the cheering message can be sent without any further input from the current user, or a text entry interface can be presented to allow the current user to define text to be included in the cheering message.

A button 506 is provided for generating a taunting message. When the button 506 is selected, the taunting message can be sent without any further input from the current user, or a text entry interface can be presented to allow the current user to define text to be included in the taunting message.

A button 508 is provided for generating a generic message. In response to triggering the button 508, a text entry interface is provided for allowing the current user to enter text to define the generic message.

A button 510 is provided for canceling the message type selection operation, such that no message will be generated or sent, and the message type selection interface 503 is removed from display.

FIG. 5B illustrates a confirmation of a sent message to another user of a social network, in accordance with an embodiment of the invention. The illustrated embodiment shows the result of sending a taunting message to the user Emily, based on selection of the button 506 of FIG. 5A. Following selection of the button 506, the taunting message may have been sent without further user input, or sent following an opportunity for the sending user to enter text (with a subsequent action to cause the taunting message to be sent, such as pressing a "send" button). As shown with continued reference to FIG. 5B, a confirmation dialogue 520 indicates that the sending user has taunted the user Emily.

Figure 6:
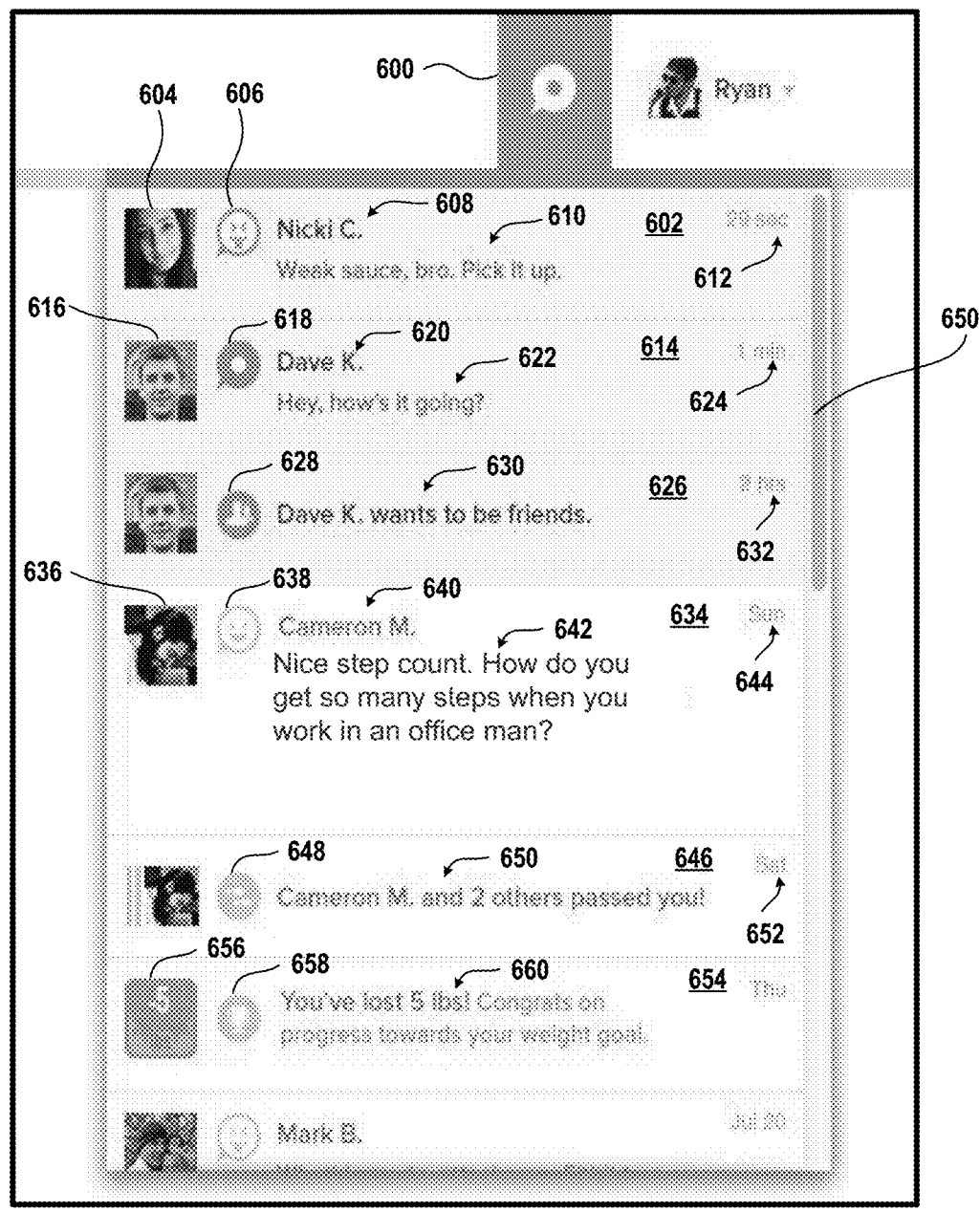
FIG. 6 illustrates an interface for viewing contents of an inbox of a user, in accordance with an embodiment of the invention.

FIG. 6 illustrates an interface for viewing contents of an inbox of a user, in accordance with an embodiment of the invention. The user's inbox includes various messages from other users, as well as system-generated notifications which inform the user about various aspects of the user's fitness related activity. In the illustrated embodiment, an inbox of a user "Ryan" is shown. The inbox is displayed in response to selection of an option 600, which triggers display of the messages in the user Ryan's inbox.

As shown, various messages/notifications are displayed in a scrollable list. A message 602 is from a user "Nicki" (ref. 608). The message 602 includes a profile picture 604 of the user Nicki. A taunting icon 606 indicates that the message 602 is a taunting message. The message 602 is further defined by text content 610, which was previously entered by the user Nicki. At ref. 612, a time is associated with the message 602, indicating when the message was sent/received. In the illustrated embodiment, the message 602 was sent/received 29 seconds ago.

A message 614 is defined from a user "Dave" (ref. 622). A profile picture 616 of the user Dave is shown, and a generic message icon 618 indicates that the message 614 is a regular or generic message (as opposed to a cheering or taunting message). The message 614 is defined by text content 622 provided by the user Dave. And a time indication 624 shows that the message 614 was sent/received approximately one minute ago.

A connection request 626 indicates that the user Dave wishes to be friends with the user Ryan on the social network (ref. 630). The request 626 includes a social icon 628, and a time indication 632 showing the request was sent/received approximately two hours ago. Upon selection or opening of the request 626, options can be provided to the user Ryan to accept or ignore the request. Acceptance of the request will cause the users Dave and Ryan to be connected on the social network, such as each user becomes a member of the other's social graph.

A message 634 is defined from a user "Cameron" (ref. 640). A profile picture 636 of the user Cameron is displayed. A cheering icon 638 indicates that the message 634 is a cheering message. The message 634 is defined by text content 642 which was entered by the user Cameron. Furthermore, a time indication 644 is shown, indicating that the message was sent/received on a prior Sunday.

In addition to messages which are defined and sent by specific users, system-generated notifications can be displayed in the listing of messages. For example, a passing notification 646 can be shown, indicating that the user Ryan has been passed by another user with respect to an activity metric. In other words, another user has attained a value for the activity metric that is superior to that of the user Ryan (value may be greater or less than that of the user Ryan depending upon the particular activity metric being compared). In the illustrated embodiment, the passing notification 646 includes an icon 648 indicating the type of activity metric is a step count. The text portion 650 of the notification 646 indicates that the user Cameron and two other users have passed the user Ryan in terms of their step counts (i.e. have achieved a higher step count than the user Ryan). A time indication 652 indicates that this occurred on a prior Saturday.

In one embodiment, passing or being passed with respect to a given activity metric may trigger an opportunity for the user to send a message to another user who has been passed, or who passed, the instant user. For example, with continued reference to FIG. 6, the notification 646 can provide access to an option to send a message to the any of the user Cameron or the two other users who have passed the user Ryan. In one embodiment, such an option is presented upon selection or interaction with the notification 646. In another embodiment, such an option is presented automatically upon viewing of the notification. In other embodiments, such an option can be presented automatically only upon the first viewing of the notification, only upon a first predefined number of viewings of the notification, or until the instant user utilizes the option to send a message.

Another system-generated notification 654 indicates that the user Ryan has lost five pounds, and congratulates the user on the progress towards a weight goal (ref. 650). A profile icon 658 is configured to indicate the loss of five pounds, and an icon 658 is configured to display a trophy.

In the illustrated embodiment, the messages and notifications are listed in reverse chronological order from top to bottom, so that the most recent messages or notifications are featured near the top of the listing. It should be appreciated that in other embodiments, the messages/notifications can be listed in any order so as to prioritize any given feature which may be associated with the messages/notifications. For example, in one embodiment, the messages may be organized according to the sending user's name, so that messages from a given user are grouped together. In another embodiment, the messages can be organized to feature those messages which are unread. In another embodiment, the messages can be organized based on predefined groups. For example, if the user is a member of a competitive group for a given fitness activity, then messages from other members of the competitive group may be collated for display. It should be appreciated that these and other methods of organizing and prioritizing a listing of messages can be combined in various configurations.

Figure 7:
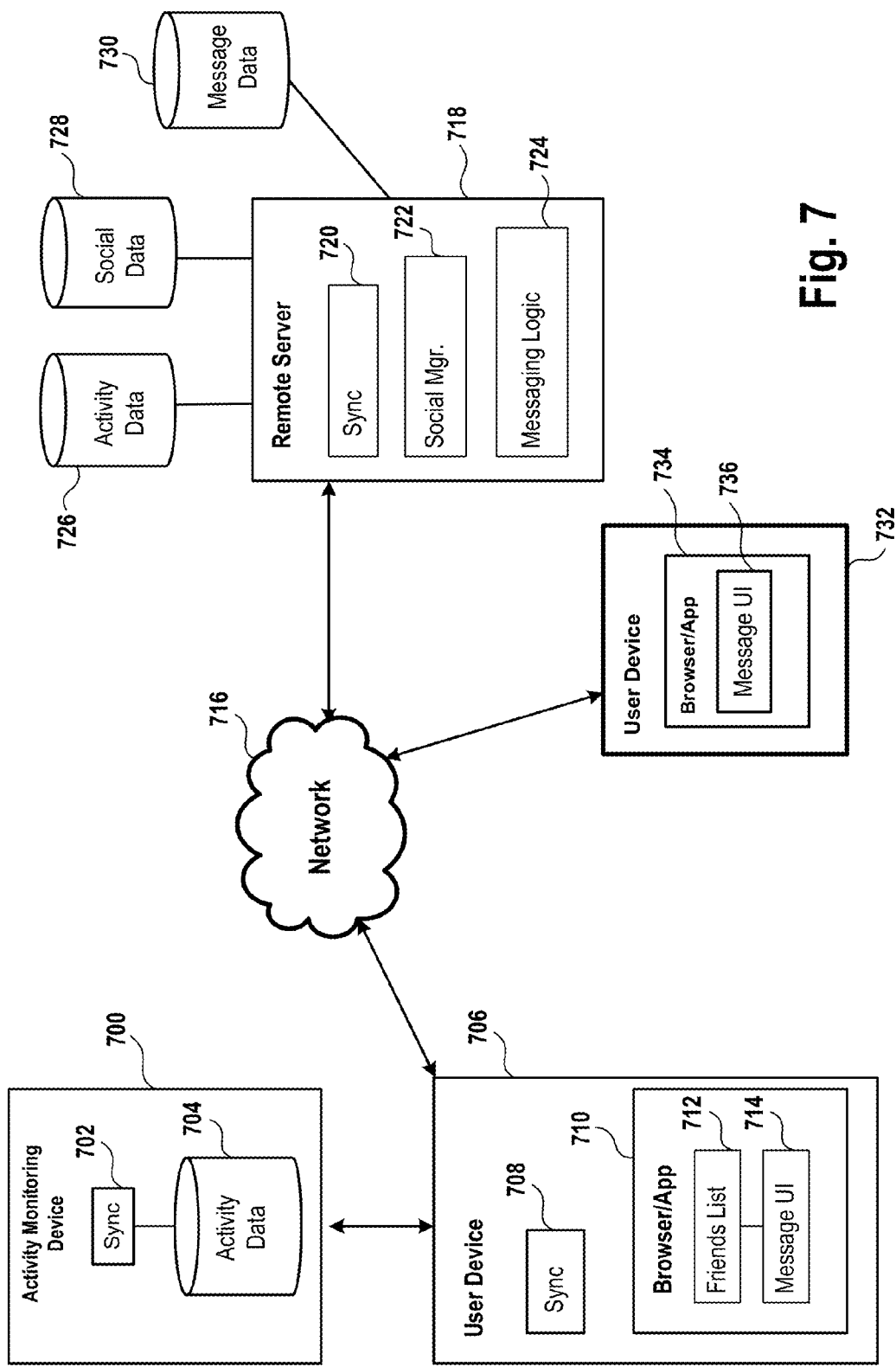
FIG. 7 illustrates a system for sending and receiving messages between users of a social network, in accordance with an embodiment of the invention.

FIG. 7 illustrates a system for sending and receiving messages between users of a social network, in accordance with an embodiment of the invention. An activity monitoring device 700 is configured to track activity of a user, as has been discussed above. An activity data storage 704 is configured to store activity data which have been detected or processed by the activity monitoring device 700. Synchronization logic 702 is configured to transmit such activity data to a user device 706, which may occur with varying frequency. The user device 706 includes synchronization logic 708 which is configured to manage receipt of the aforementioned activity data from the activity monitoring device 700, as well as manage transmission of such activity data (and data processed by the user device from such activity data) to a remote server 718 (via a network 716), the remote server 718 having synchronization logic 720 for handling receipt of such data and storing it to an activity data storage 726.

The user device 706 includes an application 710 which in various embodiments can be a dedicated application or a browser application. The application 710 is configured to provide access to the user's activity data, the social network, and provide for messaging functionality. The application 710 may retrieve (e.g. from the social data 728, via the social management logic 718) or store locally a friends list 712, which identifies friends of the user on the social network. Additionally, a messaging user interface 714 is provided for allowing the user to view messages as well as define and send messages to other users.

As alluded to above, the server 718 provides access to a social network that is defined by various social data stored to a social data storage 728. The social data includes information defining connections or other relationships between social network users, and thereby defines the social graphs of social network users. Social management logic 722 handles requests relating to the social data. For example, the application 710 may retrieve and display a news feed of current activity/posts from members of the social graph of the user. The application 710 may retrieve the news feed information by requesting it from the social management logic 722 of the remote server 718. In response to a given request, the social management logic 722 may query the social data storage 728 to both identify members of the user's social graph and retrieve posts/notifications/etc. which are related to or posted by the members of the user's social graph. In one embodiment, the social management logic 722 may also query the activity data storage 726 to retrieve activity data/metrics of members of the user's social graph. The retrieved data is returned to the application 710 for display in the social news feed at the user device 706.

It will be appreciated that the messaging user interface 714 of the application 710 may be triggered or activated from various contexts within the application 710. In one embodiment, the application 710 may be configured to allow the user to browse and view information about users in the friends list 712 (e.g. user name, date of joining the social network, activity metrics/data, etc.). When viewing information about a given friend, options may be provided to allow the user to send a message to the friend. Selection of such options may activate the messaging user interface 714 to permit the user to define and send a message to the friend. In another embodiment, the application 710 may enable viewing of a leaderboard for a given activity metric, wherein from the leaderboard, the user may access the messaging user interface 714 to send messages to the users/friends listed on the leaderboard (e.g. by selecting a given user on the leaderboard). In another embodiment, the messaging user interface 714 may be accessed from a view of a group to which the user belongs, enabling the user to send a message to another member of the group. It will be appreciated that in various embodiments, the messaging user interface 714 can be triggered or activated to permit the user to send a message to another user from any number of contexts wherein other users are identified via the application 710.

The remote server includes messaging logic 724 which is configured to handle messaging related requests and activities. For example, when a request is received to retrieve messages from the user's inbox, the messaging logic 724 retrieves the relevant messages from the message data storage 730, and returns them to the application 710 for display via the messaging UI 714. Furthermore, the messaging logic 730 receives data from the application 710 to define a new message to be sent to another user. The messaging logic 730 stores the new message based on the received data to the message data storage 730. The messaging logic 730 may also be configured to notify users when a new message has been received (e.g. send an alert/notification to the user's device).

With continued reference to FIG. 7, a second user device 732 is shown, including an application 734 (e.g. a browser or dedicated application) configured to provide a messaging UI 736. The messaging UI 736 provides the same functionality as that described with reference to the messaging UI 714. It will be appreciated that the user may access the messaging functionality described herein from any device which may access the network 716 and communicate with the server 718, and which can be configured to display the messaging UI. By way of example, in one embodiment, the user device 706 may be a mobile device such as a smart phone, whereas the user device 732 is another computing device such as a personal computer or laptop. The user may access their messages, as well as generate and send messages to other users from either device.

Figure 8:
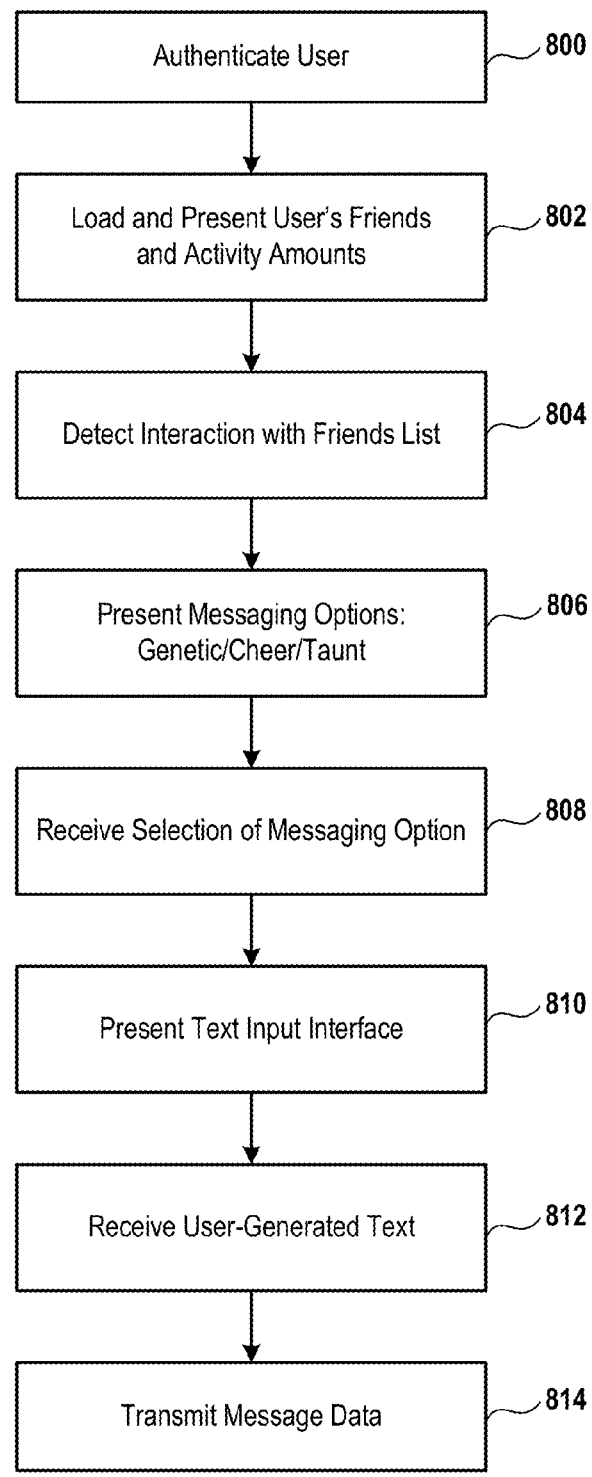
FIG. 8 illustrates a method for sending a message to user of a social network, in accordance with an embodiment of the invention.

FIG. 8 illustrates a method for sending a message to user of a social network, in accordance with an embodiment of the invention. At method operation 800, a user is authenticated or logged in to the social network. At method operation 802, one or more friends of the user (i.e. members of the user's social graph) are identified and presented in a listing/directory of friends. Additionally, activity metrics/data for each of the friends can be presented. At method operation 804, an interaction with one of the entries in the directory of friends is detected. At method operation 806, in response to the detected interaction, messaging options are presented for enabling the user to select a type of message to send to the friend with whose entry the user interacted. At method operation 808, a selection of one of the messaging options is received. At method operation 810, a text input interface is presented. At method operation 812, user-generated text is received via the text input interface. At method operation 814, the message data defined by the selected messaging option and the user-generated text is transmitted to a remote server to define a new message sent to the selected friend.

Figure 9:
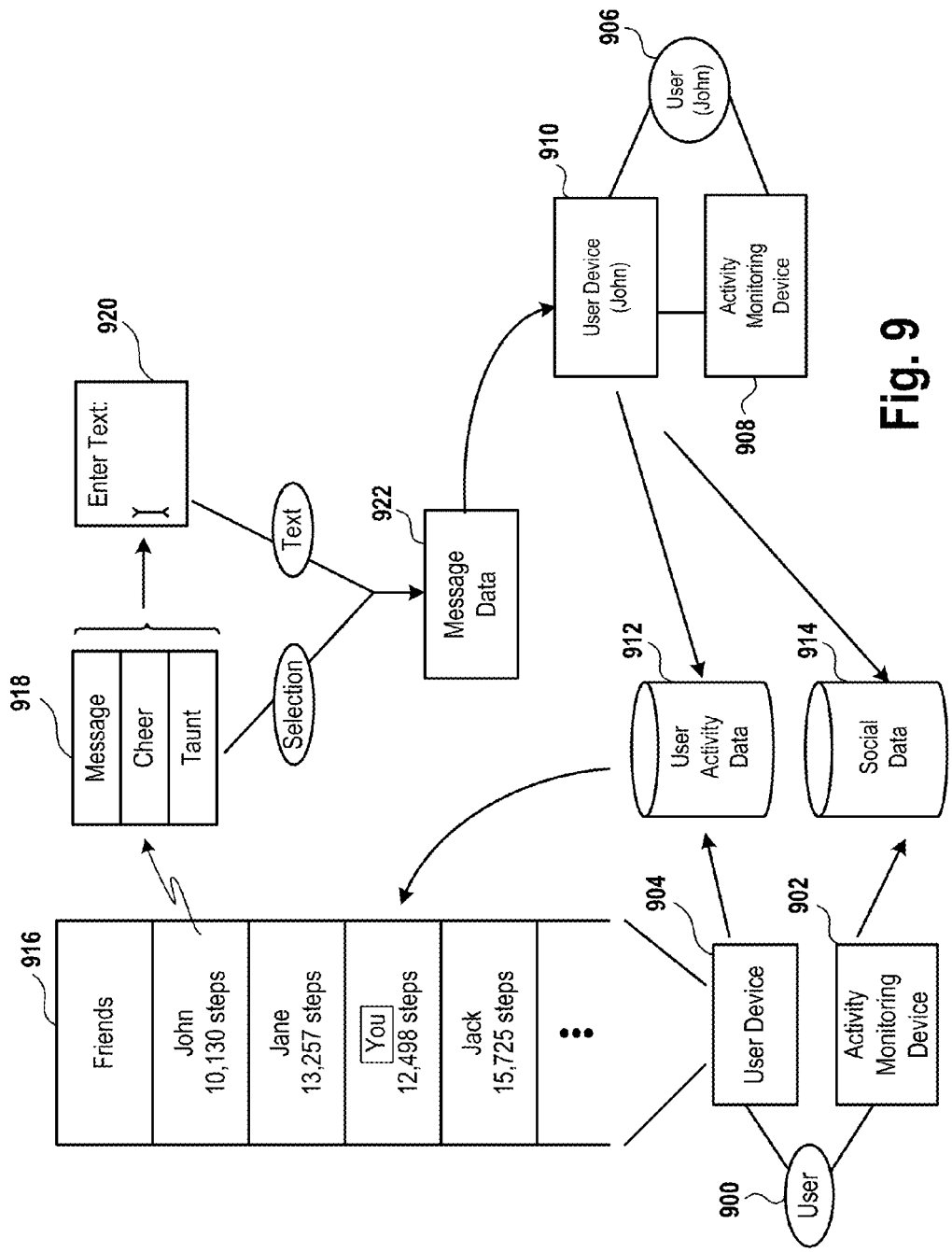
FIG. 9 conceptually illustrates sending a message from a first user to a second user, in accordance with an embodiment of the invention.

FIG. 9 conceptually illustrates sending a message from a first user to a second user, in accordance with an embodiment of the invention. In the illustrated embodiment, a user 900 operates an activity monitoring device 902 in conjunction with a user device 904. Activity data recorded by the activity monitoring device 902 can be stored to a cloud-based user activity data storage 912. Another user 906 ("John") operates an activity monitoring device 908 in conjunction with a user device 910. The activity data recorded by the activity monitoring device 908 is also stored to the user activity data storage 912. The users 900 and 906 are members of each other's social graphs, as defined in a social data storage 914.

From the user device 904, the user 900 accesses a friends list 916 which includes names of users who are members of the user's 900 social graph, including the user 906 ("John"), as well as an activity metric (e.g. a step count) associated with each user. In the illustrated embodiment, selection of the entry for the user "John" provides access to various options (ref. 918) for selecting a type of message to generate to the user "John." The options may include an option to generate a regular message, a cheering message, or a taunting message. Selection of one of the options may then provide access to a text entry field 920 to allow the user 900 to enter text to define the message. In some embodiments, separate fields are provided to enter text for a subject and a body of the message. The indicated selection of the type of message and the text input provided by the user 900 define message data 922. It should be appreciated that the message data 922 may include additional information such as the identity of the sending user (user 900), the identity of the receiving user (user 906), a time stamp, etc. The message is sent to the user 906 by storing it in association with the user's 906 inbox/account. The user 906 may view the message by accessing his/her inbox via the user device 910.

Figure 10A:
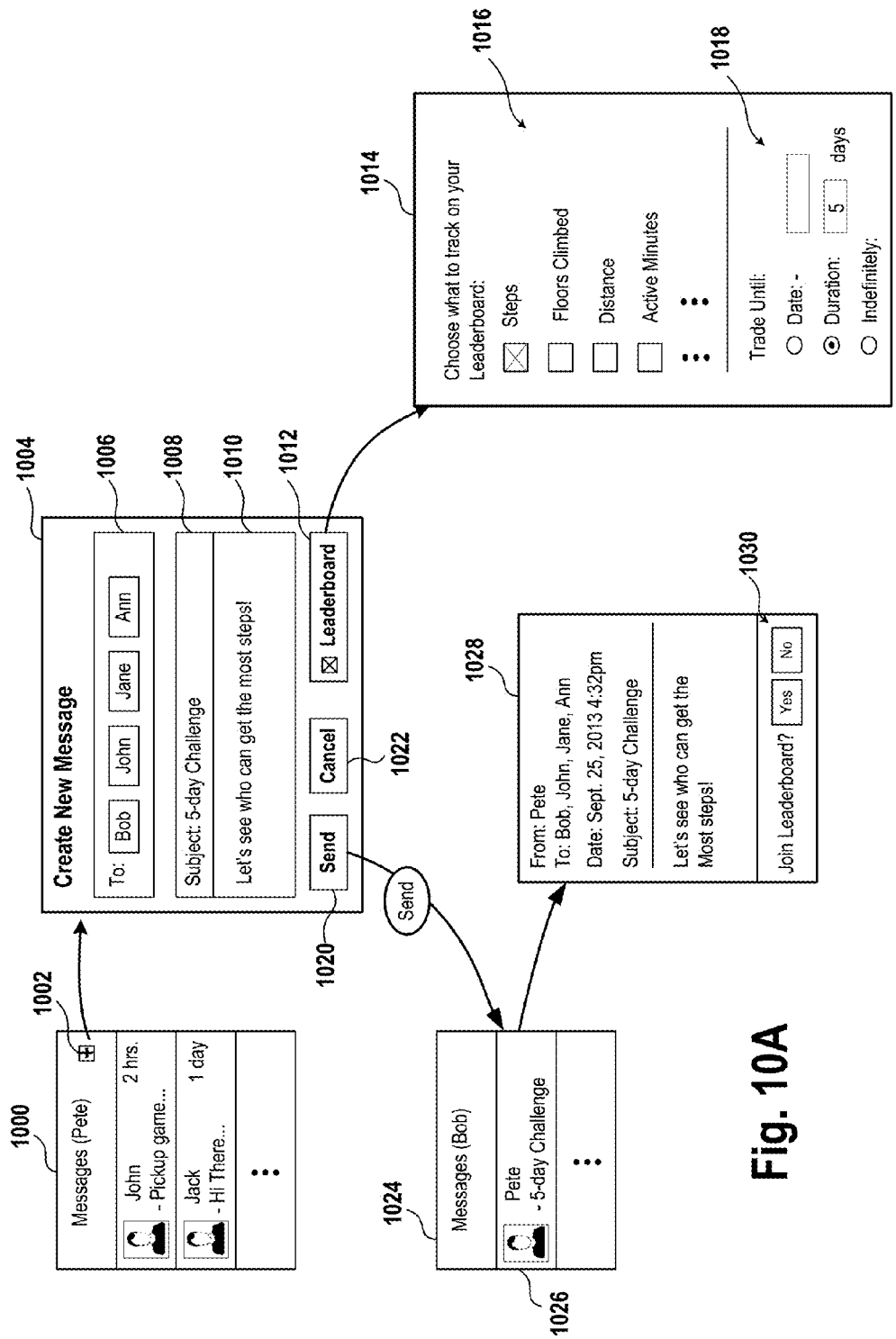
FIG. 10A conceptually illustrates generation of a leaderboard via a messaging procedure, in accordance with an embodiment of the invention.

FIG. 10A conceptually illustrates generation of a leaderboard via a messaging procedure, in accordance with an embodiment of the invention. An inbox view 1000 shows messages in an inbox for a user Pete. A new message button 1002 is selected to access a message creation interface 1004 for creating a new message. The message creation interface 1004 includes a recipient field 1006 wherein recipients of the new message may be entered (e.g. utilizing an identifier such as a user name, address, etc.). In the illustrated embodiment, the sending user (Pete) has designated the users "Bob," "John," "Jane," and "Ann" to receive the new message. A subject field 1008 is provided for the sending user (Pete) to enter a subject for the message; and a body field 1010 is provided for the entry of text to define the body of the message.

Additionally, a leaderboard option (ref. 1012) is provided whereby the sending user may opt to generate a leaderboard for an activity metric that will be associated with the message (and any thread of messages generated based on the new message). Selection of the leaderboard option provides access to a leaderboard definition interface 1014 that is configured to allow the sending user to define specifics for the leaderboard. For example, in the illustrated embodiment, the sending user may select what activity metric the leaderboard will track (ref. 1016), such as steps, floors climbed, distance traveled, active minutes, etc. In the illustrated embodiment, the sending user has selected the leaderboard to track a number of steps. It will be appreciated that more than one activity metric can be designated for tracking on the leaderboard. The sending user may also determine a duration for which the leaderboard will be active, such as until a specific date, for a predefined duration, or indefinitely. In the illustrated embodiment, the sending user has defined the leaderboard to be active for a duration of five days.

The message creation interface 1004 further includes a button 1020 to send the new message, and a button 1022 to cancel the new message. After the message is sent, the message will appear in the inbox view 1024 of the user Bob who is a recipient of the message. By selecting the message preview 1026, an entire view of the message (ref. 1028) is accessed. The message 1028 includes an option (ref. 1030) to join the leaderboard. In the illustrated embodiment, buttons for indicating yes or no are provided (ref. 1030) whereby the user Bob may indicate whether he wishes to join the leaderboard.

It will be appreciated that those users who respond positively to the request to join the leaderboard will be members of a competitive group that has been formed based on the message sent by the user Pete. The leaderboard can be displayed in conjunction with viewing of a message that is a part of the message thread (that is defined by the first message sent by the user Pete and any subsequent replies, or replies to replies). Those users that respond positively to the request to join the leaderboard will have their activity metric for which the leaderboard is defined (e.g. step count) tracked on the leaderboard and made available to other members of the competitive group, and they will likewise be able to see other members' activity metrics on the leaderboard.

Figure 10B:
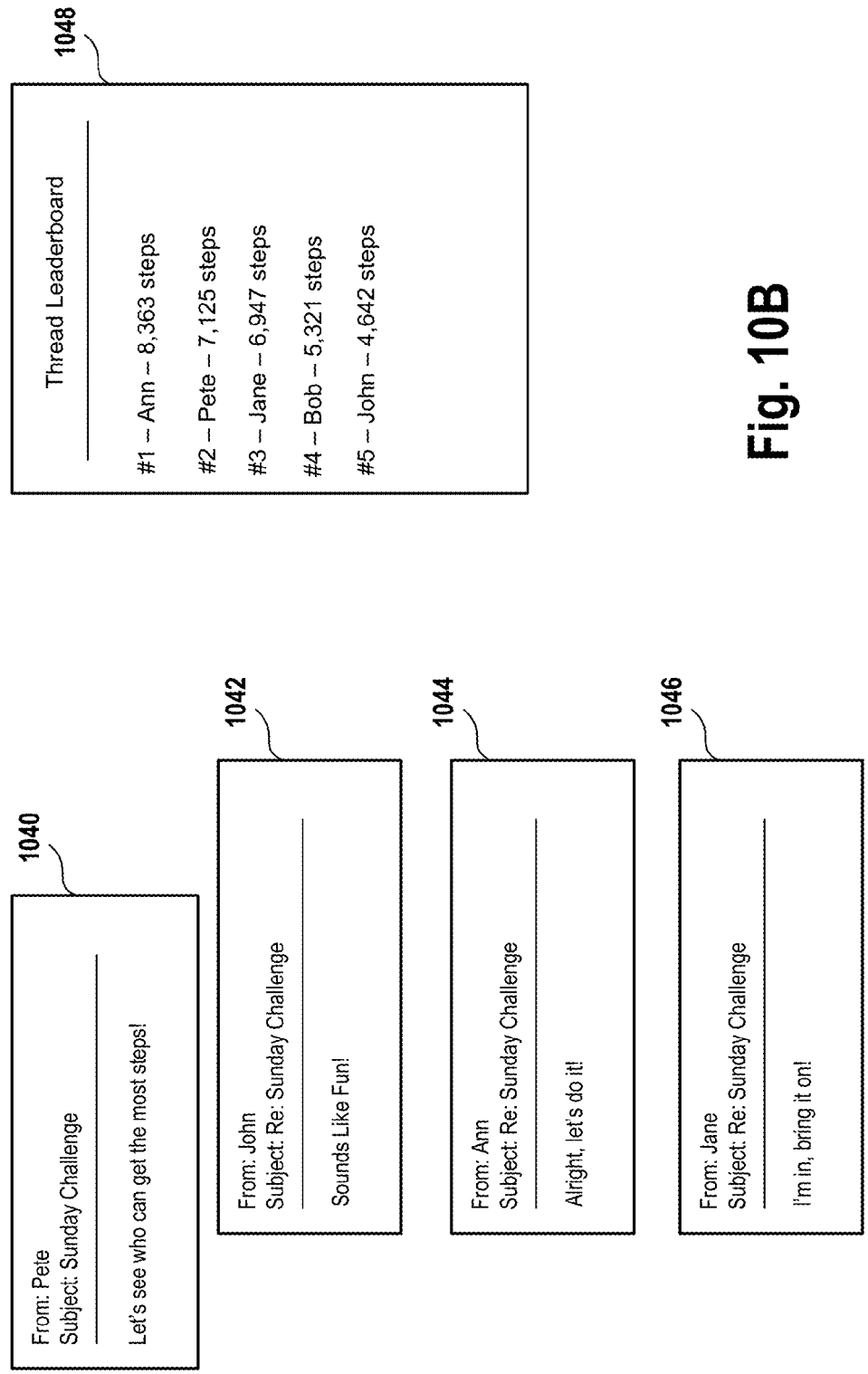
FIG. 10B illustrates a view of a message thread and accompanying leaderboard, in accordance with the embodiment of FIG. 10A.

FIG. 10B illustrates a view of a message thread and accompanying leaderboard, in accordance with the embodiment of FIG. 10A. Shown at left is a message thread defined by the original message sent by the user Pete (ref. 1040) and several replies, including messages 1042, 1044, and 1046. The associated leaderboard 1048 is shown at right, and includes the names of the users that have responded positively to the request to join the leaderboard, and displays the users in a ranked order from highest step count to lowest.

Figure 10C:
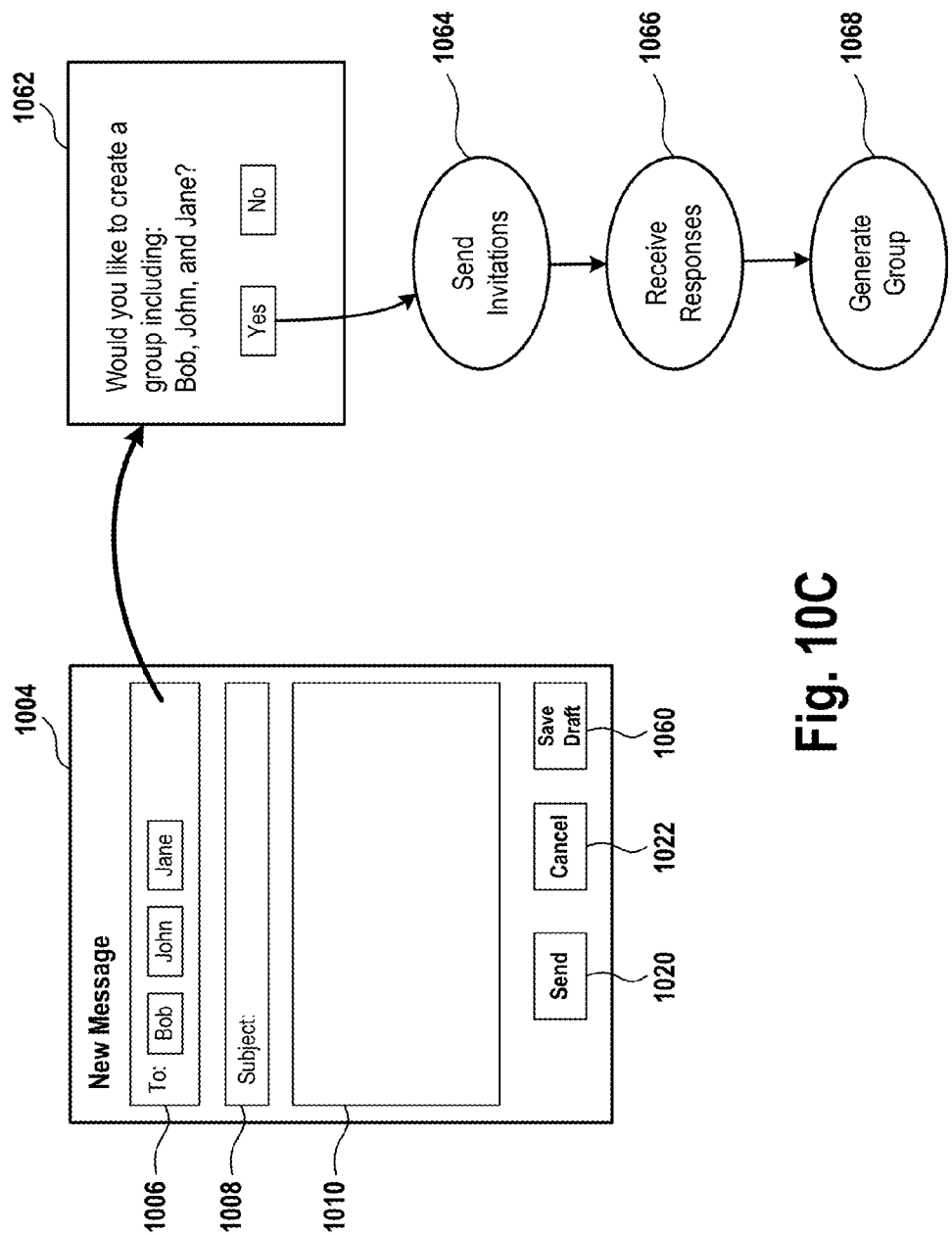
FIG. 10C conceptually illustrates creation of a competitive group based on an amount of messaging between users, in accordance with an embodiment of the invention.

FIG. 10C conceptually illustrates creation of a competitive group based on an amount of messaging between users, in accordance with an embodiment of the invention. A messaging system can be configured to determine a quantity or amount of messaging from a given user to other users, and when the quantity exceeds a predefined threshold, present an option for the given user to define a competitive group to include the given user and the other users. In the illustrated embodiment, the message creation interface 1004 is shown, similar to that shown and described with reference to FIG. 10A. A recipient field 1006, a subject field 1008, a body field 1010, a send button 1020, a cancel button 1022, and a save draft button 1060 are provided.

In response to detecting that the sending user has entered the names of users in the recipient field 1006 whom the sending user messages frequently (or whom the sending user has messaged many times), then an option to form a group including the recipients is displayed (ref. 1062). Upon activation of the option, invitations are sent to the other users to join the group (ref. 1064). Based on received responses to the invitations (ref. 1066), the group is generated (ref. 1068).

It should be appreciated that a user's messaging history may be analyzed in various ways to determine when to provide the option to form a group. For example, in one embodiment, when a user has messaged the same plurality of users a given number of times that exceeds a predefined threshold, then the option may be provided upon the next instance where the user creates a message designating the plurality of users as recipients. In one embodiment, the option to form a group is presented when a user has messaged the same users with a frequency or rate that exceeds a predefined threshold frequency or rate.

Additionally, the group that is formed may be a competitive group for which membership provides access to values of an activity metric for each of the members of the group. A leaderboard may be accessed by the members of the competitive group, and may display a ranked ordering of the members of the group based on their respective activity metric values.

Figure 11:
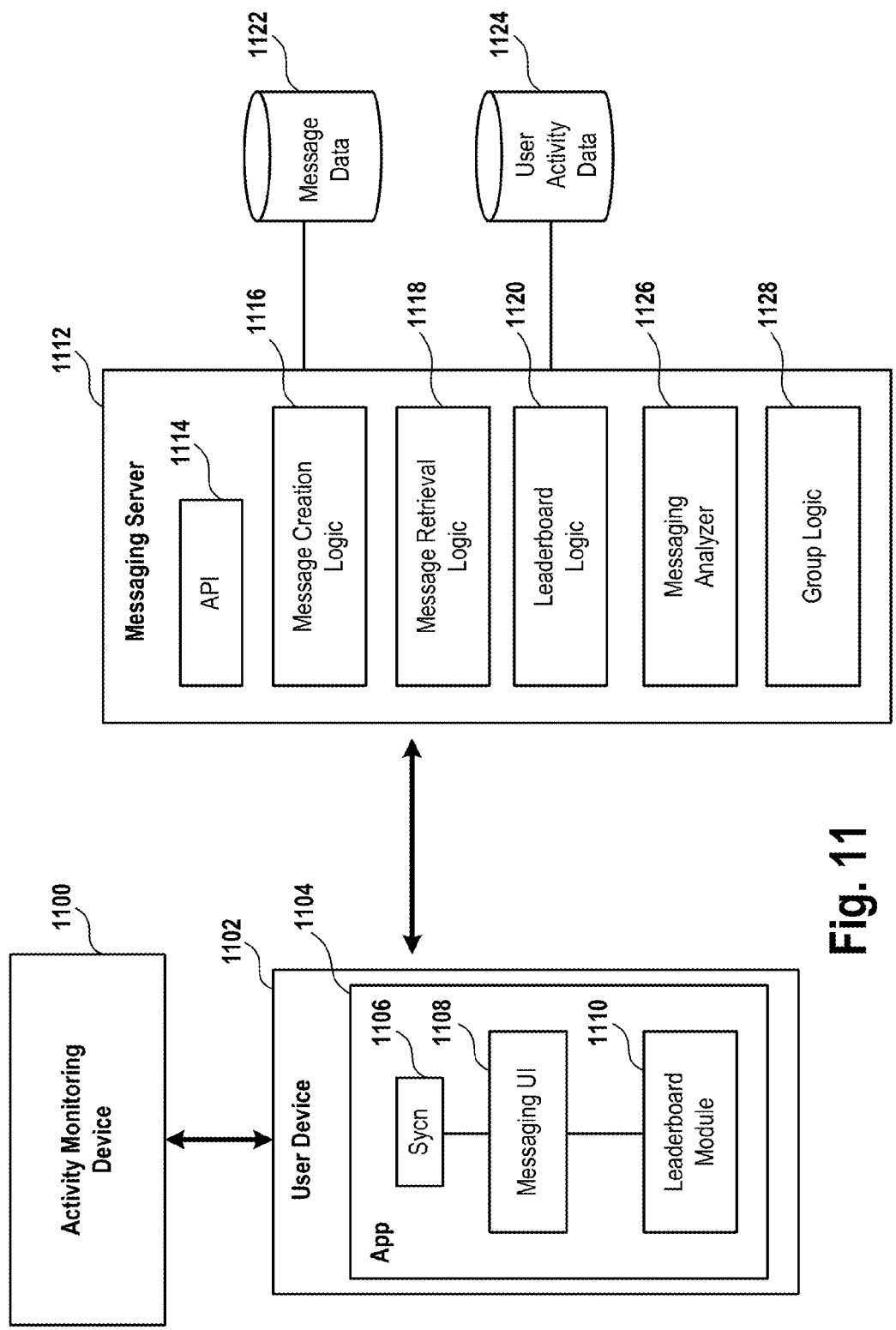
FIG. 11 illustrates a system for providing leaderboard functionality in conjunction with messaging, in accordance with an embodiment of the invention.

FIG. 11 illustrates a system for providing leaderboard functionality in conjunction with messaging, in accordance with an embodiment of the invention. An activity monitoring device 1100 interfaces with a user device 1102. The user device 1102 is configured to execute an application 1104 including a synchronization module 1106 for syncing data from the activity monitoring device 1100 to a cloud-based user activity data storage 1124. A messaging UI 1108 provides for the viewing of messages from an inbox of the user, as well as generation of new messages that are sent to other users. A leaderboard module 1110 is provided for enabling the user to define parameters for a leaderboard that is to be associated with a given message to be sent, and also provides for retrieval and viewing of a leaderboard that is associated with a given message thread.

The messaging server 1112 defines an API 1114 for accessing data such as message data defined in a message data storage 1122, and user activity data defined in the user activity data 1124. Message creation logic 1116 is provided for managing the generation of new messages. Message retrieval logic 1118 is provided for responding to requests to retrieve messages for a given user. Leaderboard logic 1120 is configured to generate a leaderboard that is to be associated with a given message thread. For example, the leaderboard logic 1120 can be configured to generate a leaderboard based on responses to requests to join a given leaderboard which have been sent to one or more users, as previously described.

The server 1112 may further define a messaging analyzer 1126 which is configured to analyze a user's messaging history to determine the quantity of messaging occurring between a given user and other users. The quantity of messaging can be defined by a number of messages sent, a frequency of messaging, or other metrics which quantify the messaging between the given user and other users.

Group logic 1128 is provided for handling group generation and management, including providing an option to generate a group when a given user's messaging to specific users exceeds a predefined threshold. The group logic 1128 may send invitations to join a group, and generate the group based on the received responses to the invitations.

In some embodiments, methods and systems are provided for identifying interesting, unusual, or otherwise significant activity by a user of an activity tracking device, and delivering messages that are related to the identified activity. Broadly speaking, a user's activity metrics/data can be analyzed to identify characteristic activity levels or patterns, and deviations from the characteristic activity levels or patterns can be identified. In response to the identification of such deviations, messages can be generated and sent to the user.

Figure 12A:
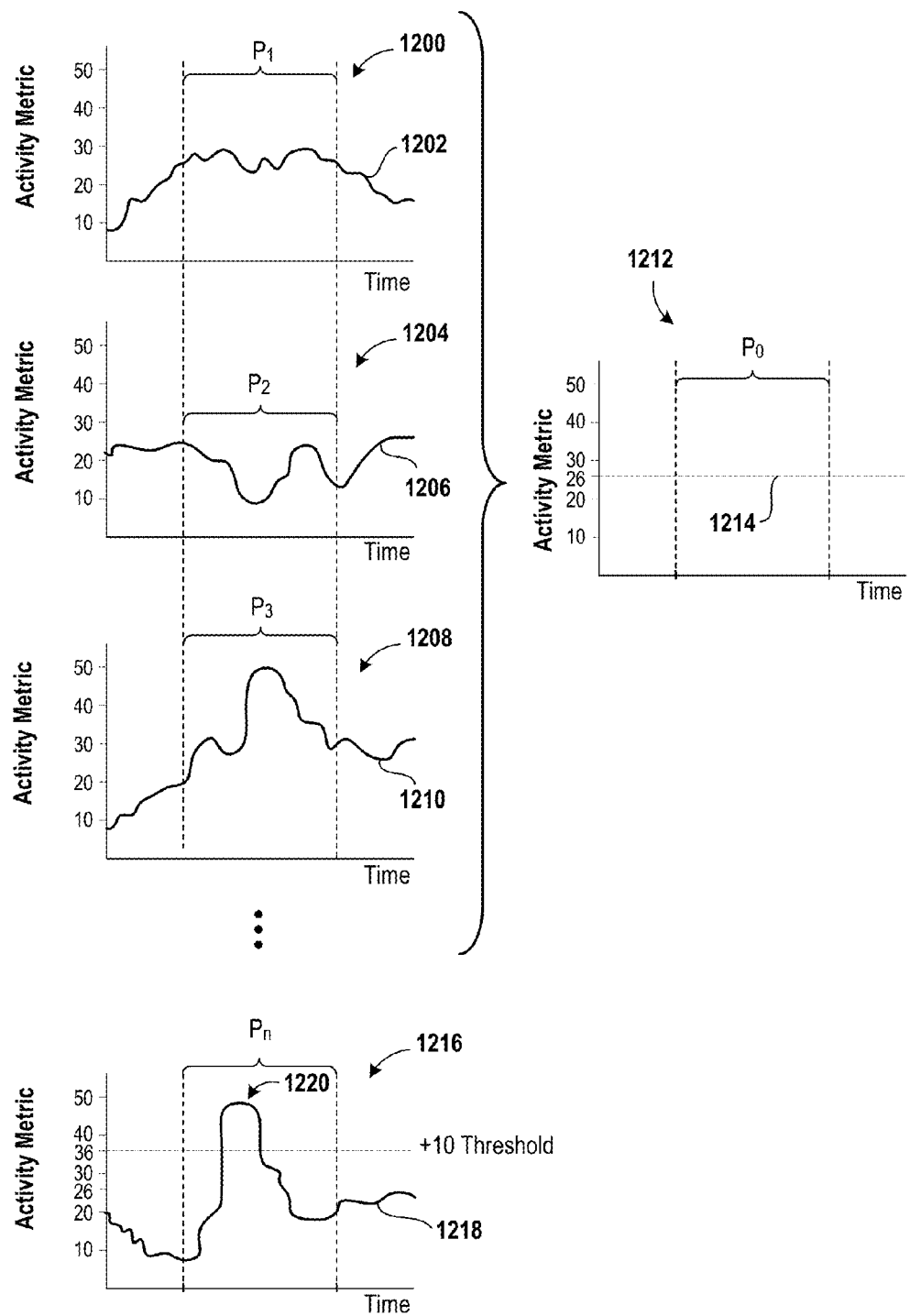
FIG. 12A conceptually illustrates determination of characteristic activity levels for a given time period, and the application thereof to identify unusual activity, in accordance with an embodiment of the invention.

FIG. 12A conceptually illustrates determination of characteristic activity levels for a given time period, and the application thereof to identify unusual activity, in accordance with an embodiment of the invention. Each of the graphs 1200, 1204, and 1208 illustrates an activity metric versus time for a given user. In the graph 1200, the activity metric over time is represented by the curve 1202; in the graph 1204, the activity metric over time is represented by the curve 1206; and in the graph 1208, the activity metric over time is represented by the curve 1210. As shown, time periods $P_1$, $P_2$, and $P_3$ are identified in the graphs 1200, 1204, and 1208, respectively.

The time periods $P_1$, $P_2$, and $P_3$ are analogous, similar, or recurrent time periods that have a same or similar time frame. That is, the time periods have a common temporal characteristic. By way of example, without limitation, each of the time periods may be the same or similar in any of the following respects: time of day (e.g. mornings, afternoons, evenings, etc.), timespan as defined by start time of day and end time of day (e.g. 6 am to 9 am), duration (e.g. hours, days, weeks, months, years), day(s) of the week (e.g. Mondays, weekdays, weekends, etc.), day(s) of the month (e.g. $1^{st}$ day of the month), week(s) of the month, month(s) of the year, etc.

It will be appreciated that in addition to time periods $P_1$, $P_2$, and $P_3$, there may be additional time periods having the same or similar time frame. The activity metric values for each of these time periods can be processed to determine a characteristic activity level for the recurrent time period, which is indicated by the curve 1214 shown at graph 1212. The characteristic activity level defines characteristic, expected, predicted, normal or otherwise typical activity metric values or levels for the time period. In the illustrated embodiment, the characteristic activity level for the generic period of time $P_0$ is represented by the curve 1214, and more specifically, has been determined to have a value 26. It should be appreciated that the units supplied with reference to the activity metric are arbitrary and provided for purposes of illustration.

In one embodiment, the characteristic activity level is defined by an average or mean of the activity metric values of the periods of time. In some embodiments, this can be conceptualized as the sum of the areas under the curves 1202, 1206, 1210, etc. during the respective periods of time P1, P2, P3, etc. and divided by the number of the time periods considered and the duration of a given generic time period. In other embodiments, the characteristic activity level is defined by a median or mode of the activity metric values of the periods of time. In other embodiments, any known method for determining characteristic activity levels may be applied that defines characteristic, expected or typical activity metric value(s) for the time period.

In some implementations, the characteristic activity metric level is defined by a singular overall value for the time period (as in the illustrated embodiment). However, in other implementations, characteristic activity metric levels can be defined with greater granularity ranging from the entirety of the time period (resulting in the aforementioned singular overall value) to any temporal subdivision of the period of time, to being continuously defined. In some implementations, a minimum temporal subdivision for the period of time may be defined based on a minimum time duration for which an activity metric value can be determined. In some embodiments, the characteristic activity levels can be determined by averaging or characterizing the activity metric curves together to define an average or characteristic curve.

With continued reference to FIG. 12A, at a graph 1216, an activity metric curve 1218 during a recent similar period of time $P_n$ is shown. The user's activity as defined by the curve 1218 is compared against the characteristic activity level to identify unusual activity. In some embodiments, when the activity metric value exceeds the characteristic activity level by a threshold amount, then unusual activity is identified, and a message that includes descriptive information about such an event can be generated and sent to a user's account. In the illustrated embodiment, a threshold value of 10 units above the characteristic activity level value of 26 is shown. That is, when the activity metric values exceed 36 units, then an unusual activity is detected, and a message can be generated and sent. In the illustrated embodiment, the activity metric exceeds 36 units, and so a message identifying this event can be generated and sent to the user.

Figure 12B:
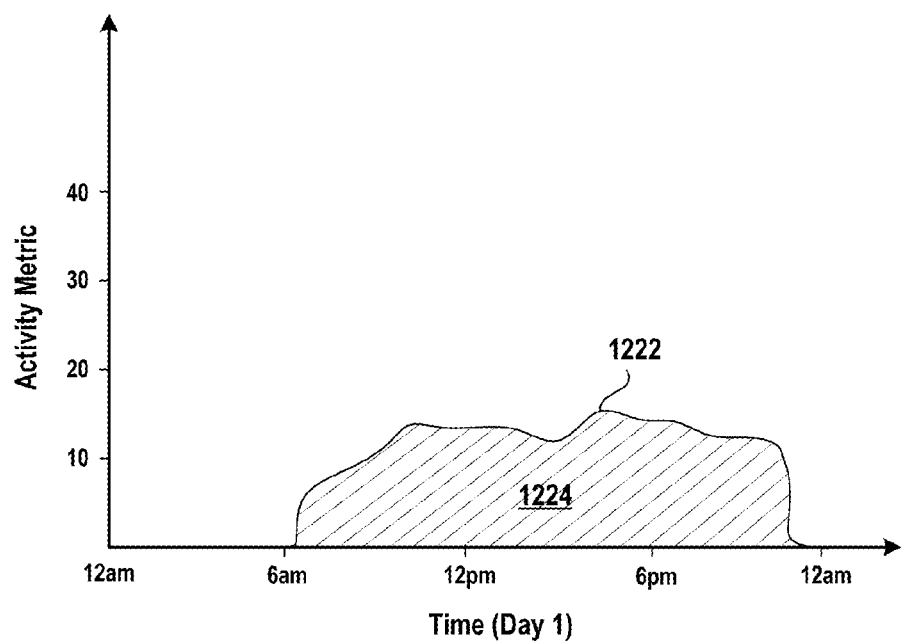
FIGS. 12B and 12C illustrate activity levels for a user on two different days, in accordance with an embodiment of the invention.
Figure 12C:
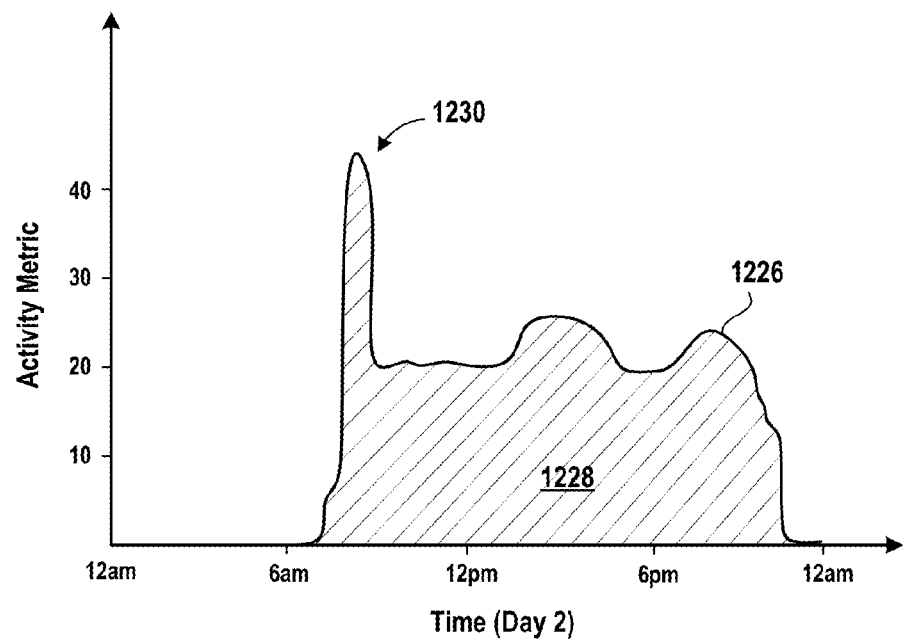

FIGS. 12B and 12C illustrate activity levels for a user on two different days, in accordance with an embodiment of the invention. In FIG. 12A, a curve 1222 defines activity metric value versus time for a first day. In FIG. 12B, a curve 1226 defines activity metric value versus time for a later second day. The activity metric levels for each of the first day and the second day can be analyzed and compared with each other.

It will be appreciated that the first day and the second day can be any two days for which activity data of the user are recorded (e.g. two days in succession, two of the same day of the week (e.g. two Saturdays), etc.). The activity metrics of the two days can be compared to identify interesting differences or changes from the first day to the second day. For example, in the illustrated embodiment, on the second day, as shown at reference 1230, the user's activity level in the morning is greatly increased as compared to that of the first day. Furthermore, the total activity amount for the second day is greater than that of the first day (conceptualized as the area 1228 under the curve 1226 for the second day versus the area 1224 under the curve 1222 for the first day.

Figure 12D:
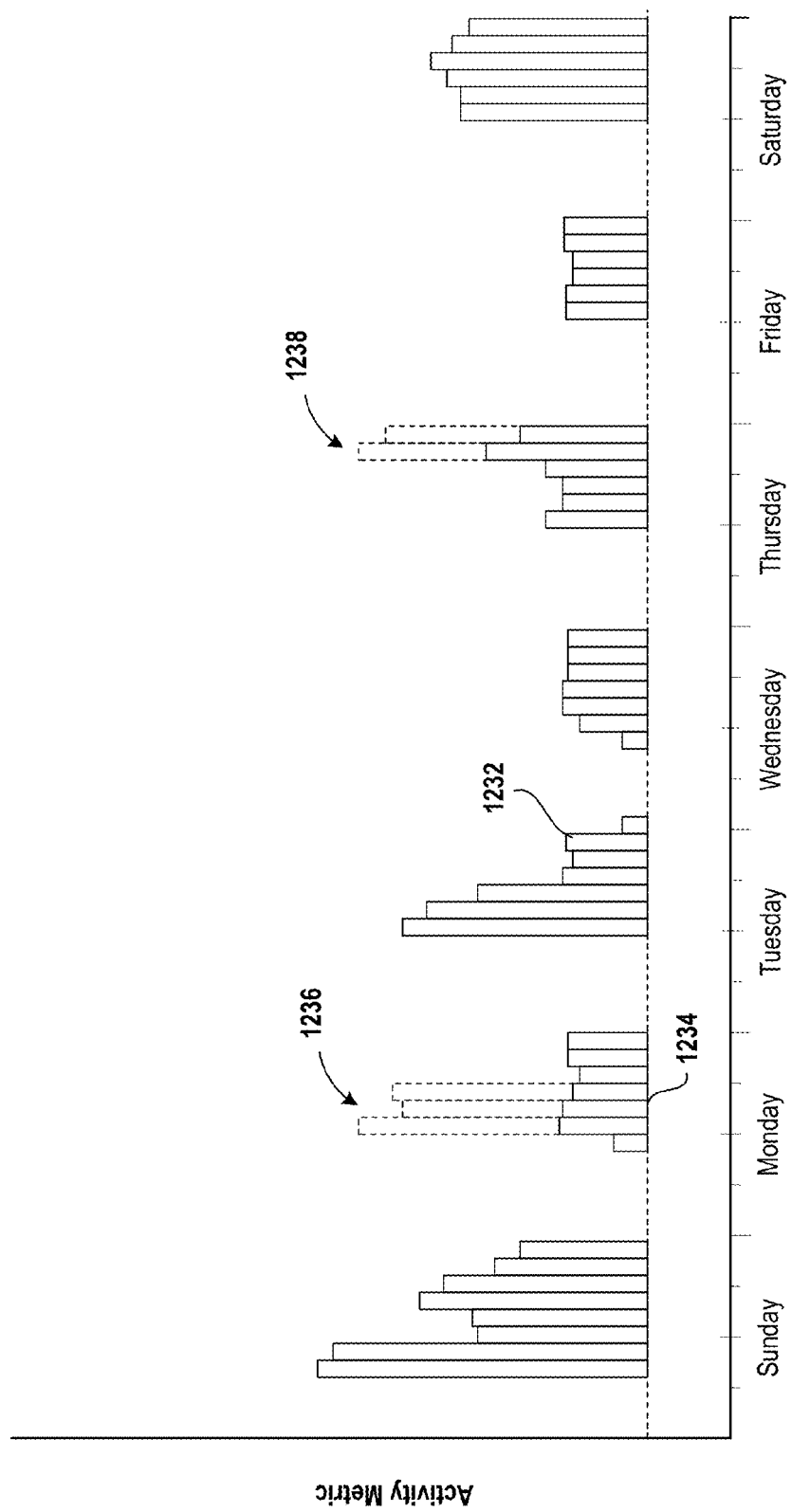
FIG. 12D illustrates a graph showing characteristic activity levels for a week, in accordance with an embodiment of the invention.

FIG. 12D illustrates a graph showing characteristic activity levels for a week, in accordance with an embodiment of the invention. A curve 1232 indicates characteristic activity levels for a user over time, for a given activity metric. As can be seen, the activity levels generally follow a pattern of periods of activity during each day, separated by periods of minimal activity, when the user is asleep. During sleep, there is a minimal activity level indicated in the graph by the baseline 1234.

Deviations from the characteristic activity levels on a given day can be detected. For example, as indicated at reference 1236, the user may exhibit a level of activity on a Monday that is substantially greater than the characteristic activity level for that time. Upon detection of such activity, a message identifying and/or describing the deviation from normal activity levels can be sent to the user. As another example shown in the illustrated graph, the user's activity level on a Thursday may typically include elevated activity levels on Thursday nights (e.g. user plays basketball on Thursday nights). However, on a given Thursday, the elevated activity level may be even greater than normal, as indicated at reference 1238. In response to detection of this occurrence, a message can be generated and sent to the user, identifying and describing the activity.

The threshold for detection of unusual activity can be context dependent. For example, the threshold for detection of unusual activity for the time period at reference 1236, when activity levels are normally not especially elevated, can be greater than the threshold for detection for the time period at reference 1238, when it is expected that activity levels will already be elevated, and hence even higher elevated activity levels may be considered significant at a lower threshold relative to the already elevated activity levels.

Messages which are generated in response to detection of interesting or unusual activity can be customized to include relevant activity metrics/data that is descriptive of the activity (e.g. "You improved on yesterday's stepcount by 1000 steps," "You're only 500 steps from beating last week's total", etc.). Generated messages which are descriptive of the unusual activity are sent to a user account associated with the user. Throughout the present disclosure, messages are described as being sent to users for ease of description, though it will be understood that this includes sending the messages to user accounts that are associated with the users. Messages can be sent via any of a variety of messaging technologies including, but not limited to, private messages, e-mail, push notifications, etc. Additionally, messages may be sent to additional users who are members of the primary user's social graph.

It will be appreciated that detection of interesting or unusual activity may be determined according to any of various methods and techniques. Broadly speaking, activity data for first and second periods of time, which have a similar time frame, can be analyzed to determine characteristic activity levels for the periods of time. These may be compared to determine deviations between the two periods of time, and so identify interesting or unusual activity by a user. For example, in one embodiment, a historic mean level of activity is determined, and deviations from the historic mean can be detected. In other embodiments, other statistical measures of characteristic activity levels can be determined (e.g. median, mode, etc.) and deviations therefrom can be detected to identify interesting or unusual activity. It will be appreciated that in some embodiments, such deviations are detected for current and/or recent time periods which are subsequent to the time period from which the historic mean is calculated, so as to provide feedback to the user regarding their current/recent activity. A deviation can be defined in various ways, such as a difference exceeding a predefined amount, a predefined threshold, a predefined fractional amount (e.g. difference exceeding a specified percentage difference), a predefined number of standard deviations, etc. In still other embodiments, any known method for identifying a statistically significant difference can be applied to activity data of a user to identify unusual activity.

In accordance with additional embodiments, group events can be defined in which two or more users participate based on their activity data. Examples of group events include challenges or races, in which users compete against one another to achieve a highest or otherwise best activity amount or other activity related outcome, missions in which users each have individual goals that are pursued together in the context of the group, and group goals where users collectively pursue a goal.

Figure 13A:
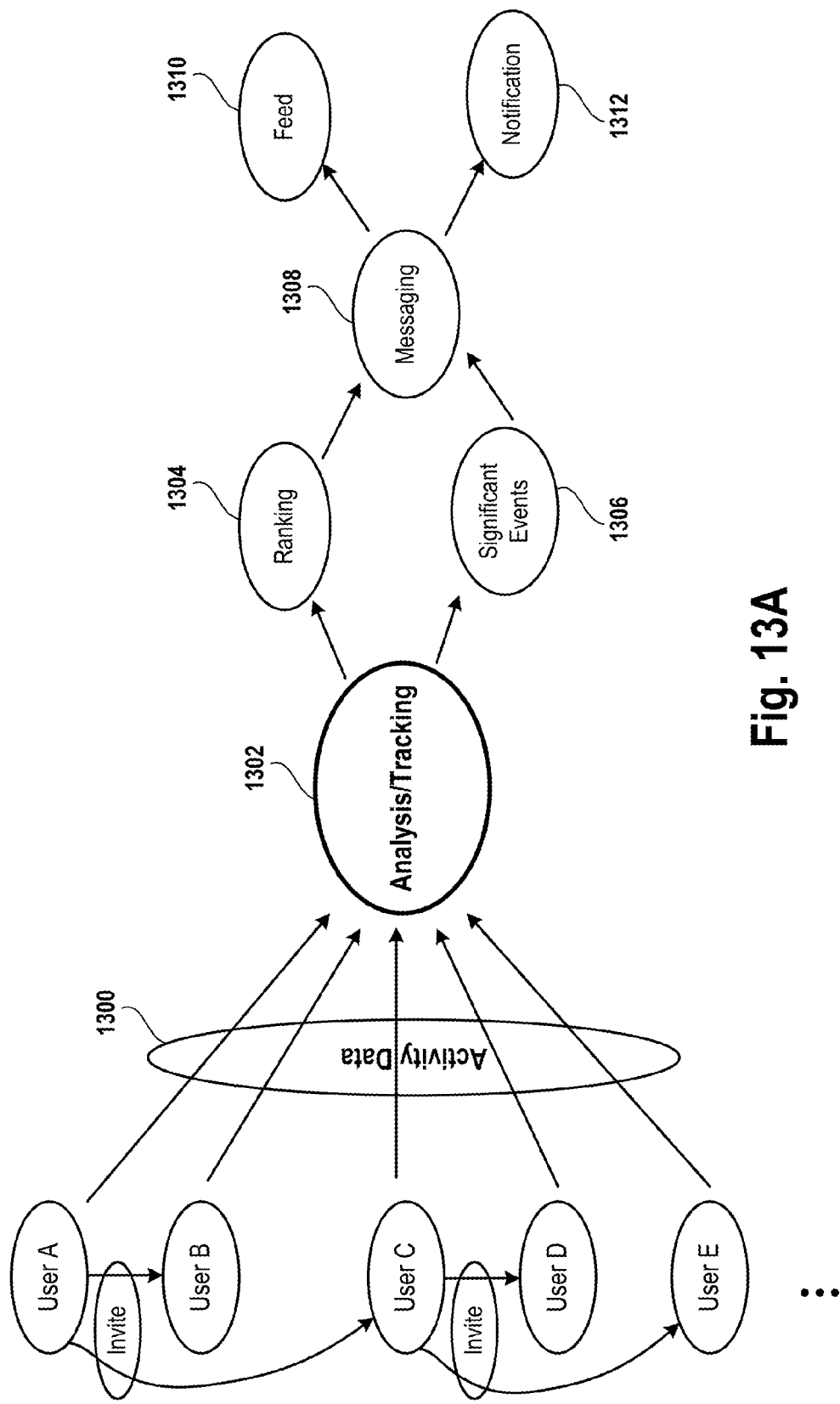
FIG. 13A is a flow diagram conceptually illustrating messaging generated for a group event, in accordance with an embodiment of the invention.

FIG. 13A is a flow diagram conceptually illustrating messaging generated for a group event, in accordance with an embodiment of the invention. In the illustrated embodiment, a user A invites user B and user C to the group event, and user C in turn invites user D and user E to the group event. Upon joining the group event activity data 1300 for the users is analyzed and tracked for purposes of the group event, as indicated at reference 1302. Based on the analysis and tracking, the users can be ranked 1304, and significant events can be detected 1306. Based on the ranking and significant events, messages can be generated 1308, and propagated as notifications 1312 to some or all of the users, as well as to a message feed 1310 defined for the group event.

Figure 13B:
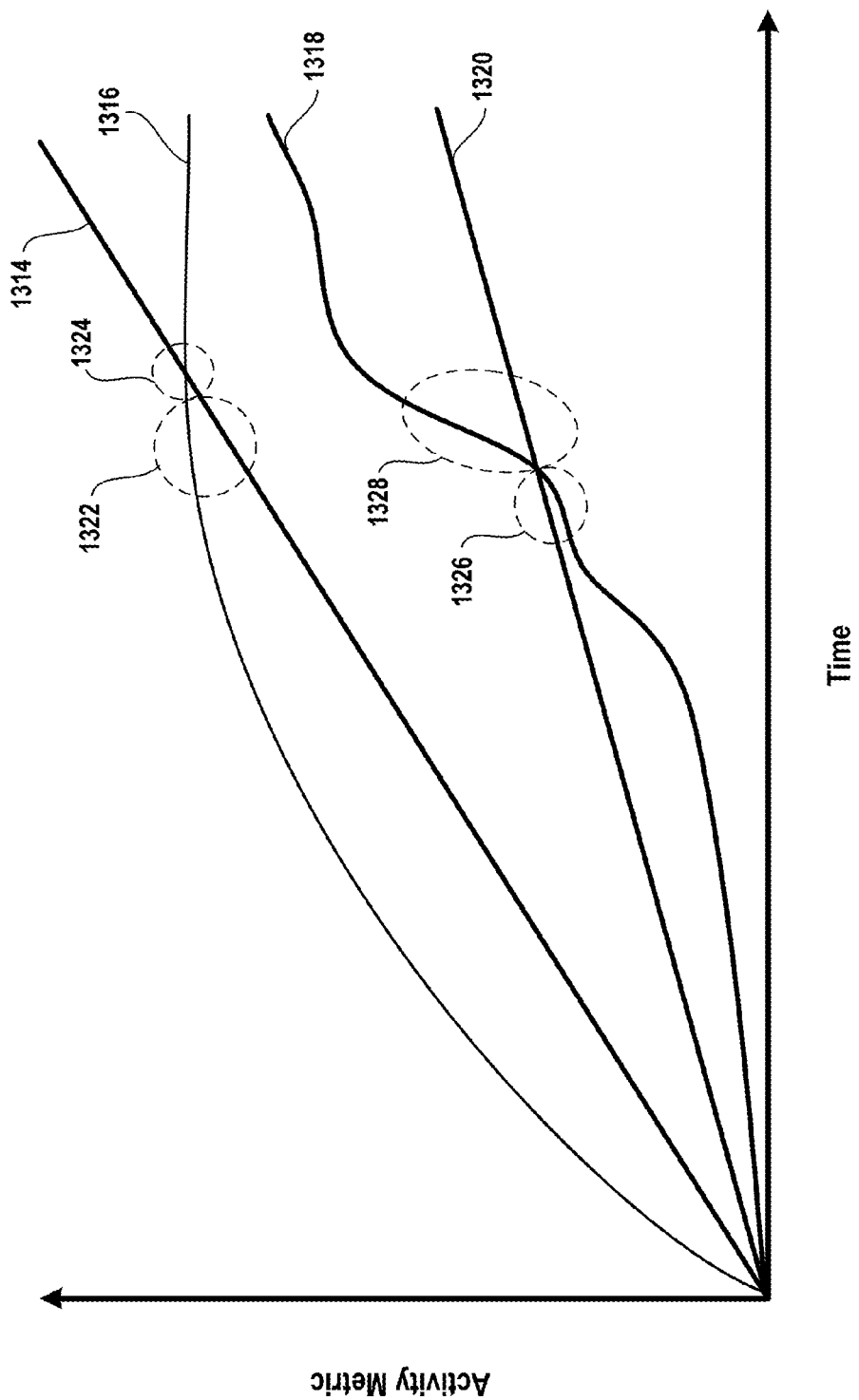
FIG. 13B illustrates a graph of activity metric versus time for a group event, in accordance with an embodiment of the invention.

FIG. 13B illustrates a graph of activity metric versus time for a group event, in accordance with an embodiment of the invention. Each of the curves 1314, 1316, 1318, and 1320 indicates activity metric values/levels for users A, B, C, and D, respectively. During the course of the group event, each of the users is ranked based on their activity metric values/levels. Interesting activity occurring during the group event that indicates a changes in relationship between two or more of the users can be identified, and in response, messages can be generated and sent to user accounts that are associated with the users. For example, at reference 1322, the activity level for user A is about to surpass that of user B. Upon detection of such an event, a message can be generated indicating as such (e.g. "User A is gaining on User B and about to pass!"). Furthermore, the message may be customized based on the intended recipient. For example, the message to user A may be "Keep it up! You're about to pass User B!" Whereas, the message to user B may be "Watch out! User A is on your heels and gaining fast!"

When a passing event is detected in which the activity value/level of one user surpasses that of another, messages can also be generated and sent. With continued reference to FIG. 13B, at reference 1324, the activity level for user A passes that of user B. Upon detection of the passing event, a message can be generated identifying and/or describing the passing event. Again, the message can be customized based on the recipient. For example, since the passing event affects the first place ranking in the group event, this may something of interest to all participants, and therefore messages may be generated and sent to all the participants. Again, the messages may be customized based on the recipient. For example, the message to user A may be, "Congrats! You just passed user B to take first place!" Whereas the message to user B may be, "Uhoh! User A just stole first place from you!" And the messages sent to the remaining participants may be, "User A takes the lead!"

At reference 1326, the activity levels for users C and D are close to each other (differ by less than a predefined amount)

for a length of time, and this may be identified as an interesting event. This will be interesting for user C and D, but may be of less interest to the remaining participants, as users C and D are not in the top rankings. Therefore, messages are generated and sent to users C and D that identify and describe this occurrence, but messages are not sent to the other participants. By way of example, the message to user C may be, "You and User D are running neck and neck!" whereas the message to user D may be, "You and User C are running neck and neck!"

At reference 1328, the activity level of user C surpasses that of user D by a large amount (greater than a threshold amount). Therefore, upon detection of this passing event, messages can be generated and sent to users C and D. For example, the message to user C may be, "You rocketed past User D into third place!" whereas the message to user D may be, "User D rocketed past you into third place!"

It will be appreciated that there may be any number of unusual or interesting events or changes in relationship between activity levels of users, and that such may be detected, and in response, messages can be generated and sent to some or all participating users. Messages can be customized to include activity metric data that is related to or descriptive of the significant event. Several examples are described herein for purposes of illustration, without limitation.

For example, when someone takes first place with a significant lead (e.g. a user "Joe" takes lead from a user "Sally"), messages to third parties may be "Joe rocketed past Sally into first place," "Joe zoomed into first," etc. When the recipient is the actor (e.g. "Joe") the message may be "You rocketed past Sally into first place," "You zoomed into $1^{st}$," etc. When the recipient is the subject (e.g. "Sally"), the message may be "Joe rocketed past you into first place," etc. In the table below, several examples of message templates are provided for the situation when someone takes first place with a significant lead (e.g. activity metric/level exceeds the second place person by at least a threshold amount). The message templates are tailored to the recipient depending upon whether the recipient is a third party (i.e. not involved in gaining or losing first place), an actor (i.e. person who takes first place), or the subject (i.e. person who previously held first place but now lost it). The message templates can include fillable fields for insertion of the appropriate names and relevant activity metric data (indicated in braces in the table below). By way of example, the relevant activity metric data may be a total cumulative amount of the activity metric for the first place person (according to which the ranking is determined), an amount of the activity metric acquired by the person to take first place, an amount by which the first place person is in the lead, etc.

| Third Parties | Recipient is the Actor | Recipient is the Subject |
|---|---|---|
| {Joe} rocketed past {Sally} into first place | You rocketed past {Sally} into first place | {Joe} rocketed past you into first place |
| {Joe} snatched the title from {Sally} | You snatched the title from {Sally} | {Joe} snatched your title |
| {Joe} took the crown from {Sally} | You took the crown from {Sally} | {Joe} took your crown |
| {Abby} knocked {Brad} out of 1st place | You knocked {Brad} out of 1st place | {Abby} knocked you out of 1st place |
| {Abby} zoomed into 1st | You zoomed into 1st | |
| {Abby} flew past {Brad} into 1st place | You flew past {Brad} into 1st place | {Abby} flew past you into 1st place |
| {ABBY} IS IN FRONT!!! | YOU'RE IN FRONT!!! | |
| With { 23,000} steps, {Joe} just took a whale of a lead | With { 23,000} steps, you just took a whale of a lead | |
| Watch out Tony Danza, looks like {Joe} is the boss | Watch out Tony Danza, looks like you're the boss | |
| {Joe} trounced the competition | You trounced the competition | |
| {Joe} gunned it into 1st place | You gunned it into 1st place | |
| {Joe} stole the lead | You stole the lead | |
| {Joe} shot straight past the pack into 1st place | You shot straight past the pack into 1st place | |
| {Joe} took the lead . . . and boom goes the dynamite | You took the lead . . . and boom goes the dynamite | |
| Some serious steppage has occurred. {Joe}'s snagged the lead | Some serious steppage has occurred. You've snagged the lead | |

For example, when someone (e.g. user "Joe") takes first place with a modest lead, messages to third parties may be "Joe squeaked into $1^{st}$," etc. When the recipient is the actor, the message may be "You squeaked into $1^{st}$," etc. When the recipient is the subject, the message may be "Joe claimed your lead," etc. In the table below, several examples of message templates are provided for the situation when someone takes first place with a modest lead (e.g. activity metric/level exceeds the second place person by less than a threshold amount). The message templates are tailored to the recipient depending upon whether the recipient is a third party (i.e. not involved in gaining or losing first place), an actor (i.e. person who takes first place), or the subject (i.e. person who previously held first place but now lost it). The message templates can include fillable fields for insertion of the appropriate names and relevant activity metric data (indicated in braces in the table below). By way of example, the relevant activity metric data may be a total cumulative amount of the activity metric for the first place person (according to which the ranking is determined), an amount of the activity metric acquired by the person to take first place, an amount by which the first place person is in the lead, etc.

| Third Parties | Recipient is the Actor | Recipient is the Subject |
|---|---|---|
| {Abby} cruised into first place | You cruised into first place | |
| {Brad} squeaked into 1st | You squeaked into 1st | |
| {Joe} claimed the lead from {Sally} | You claimed the lead from {Sally} | {Joe} claimed your lead |
| {Brad} just demoted {Abby} to 2nd place | You just demoted {Abby} to 2nd place | {Brad} just demoted you to 2nd place |
| {Abby} took 1st place | You took 1st place | |
| {Abby} took the lead | You took the lead | |
| {Brad} was in the lead . . . but not anymore | | You were in the lead . . . but not anymore |
| {Abby} is out in front | You're out in front | |
| {Abby}'s the new leader | You're the new leader | |
| {Abby} is the new frontrunner | You are the new frontrunner | |
| {Brad} is the new leader with {23,000 steps} | You are the new leader with {23,000 steps} | |
| Leadership change: {Brad}'s in front! | Leadership change: you're in front! | |
| Look out: {Abby}'s up top | Look out: you're up top | |

For example, when someone takes Nth place with a significant lead (e.g. user "Brad" overtakes user "Abby" by 3000 steps), messages to third parties could be "Brad's in front of Abby by 3000 steps," etc. When the recipient is the actor (e.g. Brad), the message could be, "You're in front of Abby by 3000 steps," etc. When the recipient is the subject, the message could be "Brad's in front of you by 3000 steps," etc. In the table below, several examples of message templates are provided for the situation when someone takes Nth place with a significant lead (e.g. activity metric/level exceeds the next (N+1) place person by at least a threshold amount). The message templates are tailored to the recipient depending upon whether the recipient is a third party (i.e. not involved in gaining or losing Nth place), an actor (i.e. person who takes Nth place), or the subject (i.e. person who previously held Nth place but now lost it). The message templates can include fillable fields for insertion of the appropriate names and relevant activity metric data (indicated in braces in the table below). By way of example, the relevant activity metric data may be a total cumulative amount of the activity metric for the Nth place person (according to which the ranking is determined), an amount of the activity metric acquired by the person to take Nth place, an amount by which the Nth place person is ahead of the next (N+1) place person, etc.

| Third Parties | Recipient is the Actor | Recipient is the Subject |
|---|---|---|
| {Brad}'s in front of {Abby} by {3,000} steps | You're in front of {Abby} by {3,000} steps | {Brad}'s in front of you by {3,000} steps |
| {Brad} just took a {3,000} step lead over {Abby} | You just took a {3,000} step lead over {Abby} | {Brad} just took a {3,000} step lead over you |
| {Brad}'s eating {Abby}'s dust | {Brad}'s eating your dust | You're eating {Abby}'s dust |
| {Joe} leapfrogged {Sally} | You leapfrogged {Sally} | {Joe} leapfrogged you |
| {Abby} rushed past {Brad} | You rushed past {Brad} | {Abby} rushed past you |
| {Joe} took a crushing lead over {Sally} | You took a crushing lead over {Sally} | {Joe} took a crushing lead over you |
| {Brad} flew past {Abby} | You flew past {Abby} | {Brad} flew past you |
| {Brad} overtook {Abby} by {3,000} steps | You overtook {Abby} by {3,000} steps | {Brad} overtook you by {3,000} steps |
| {Abby}'s crushing {Brad} right now: {3,000} steps ahead | You're crushing {Brad} right now: {3,000} steps ahead | {Abby}'s crushing you right now: {3,000} steps ahead |
| {Abby} powered past {Brad} by {3,000} steps | You powered past {Brad} by {3,000} steps | {Abby} powered past you by {3,000} steps |
| {Brad} zoomed past {Abby} | You zoomed past {Abby} | {Brad} zoomed past you |
| {Abby} left {Brad} in the dust | You left {Brad} in the dust | {Abby} left you in the dust |
| {Brad}'s leading {Abby} by {3,000} steps now | You're leading {Abby} by {3,000} steps now | {Brad}'s leading you by {3,000} steps now |
| {Joe} just rocked {Sally}'s world | You just rocked {Sally}'s world | {Joe} just rocked your world |
| {Joe} crushed {Sally}'s step total | You crushed {Sally}'s step total | {Joe} crushed your step total |
| {Joe} just dominated {Sally}'s lead | You just dominated {Sally}'s lead | {Joe} just dominated your lead |
| {Joe} delivered a blow to {Sally} | You delivered a blow to {Sally} | {Joe} delivered you a blow |
| {Joe} beat {Sally}'s total | You beat {Sally}'s total | {Joe} beat your total |
| {Joe} swept {Sally}'s total | You swept {Sally}'s total | {Joe} swept your total |
| {Joe} just showed {Sally} what's up | You just showed {Sally} what's up | {Joe} just showed you what's up |
| {2,000} more steps shows {Joe} is playing hardball with {Sally} | {2,000} more steps shows you're playing hardball with {Sally} | {2,000} more steps shows {Joe} is playing hardball with you |

In the table below, several examples of message templates are provided for the situation when someone takes Nth place with a modest lead (e.g. activity metric/level exceeds the next (N+1) place person by less than a threshold amount). The message templates are tailored to the recipient depending upon whether the recipient is a third party (i.e. not involved in gaining or losing Nth place), an actor (i.e. person who takes Nth place), or the subject (i.e. person who previously held Nth place but now lost it). The message templates can include fillable fields for insertion of the appropriate names and relevant activity metric data (indicated in braces in the table below). By way of example, the relevant activity metric data may be a total cumulative amount of the activity metric for the Nth place person (according to which the ranking is determined), an amount of the activity metric acquired by the person to take Nth place, an amount by which the Nth place person is ahead of the next (N+1) place person, etc.

| Third Parties | Recipient is the Actor | Recipient is the Subject |
|---|---|---|
| Bad news for {Brad}. {Abby} just pulled ahead | Bad news for {Brad}. You just pulled ahead | Bad news. {Abby} just pulled ahead of you |
| {Joe} surpassed {Sally} | You surpassed {Sally} | {Joe} surpassed you |
| {Joe} outstepped {Sally} | You outstepped {Sally} | {Joe} outstepped you |
| {Joe} overtook {Sally} | You overtook {Sally} | {Joe} overtook you |
| {Joe} bumped {Sally} | You bumped {Sally} | {Joe} bumped you |
| Move over {Sally}, {Joe}'s making a play | Move over {Sally}, {yourName}'s making a play | Move over {yourName}, {Joe}'s making a play |
| {Brad}'s moving up in the world | You're moving up in the world | |
| {Abby} passed {Brad} | You passed {Brad} | {Abby} passed you |
| {Abby} tiptoed past {Brad} | You tiptoed past {Brad} | {Abby} tiptoed past you |
| {Joe} snuck past {Sally} | You snuck past {Sally} | {Joe} snuck past you |
| {Joe} slid past {Sally}'s step count | You slid past {Sally}'s step count | {Joe} slid past your step count |
| {Joe} stepped up to the bar that {Sally}'s been setting | You stepped up to the bar that {Sally}'s been setting | {Joe} stepped up to the bar that you've been setting |

In the table below, several examples of message templates are provided for the situation when two users have very close activity metrics (e.g. activity metric/level of Nth place person and next (N+1) place person is less than a threshold amount). The message templates are tailored to the recipient depending upon whether the recipient is a third party (i.e. not involved in gaining or losing Nth place) or an actor (i.e. person who holds Nth place or the next (N+1) place. The message templates can include fillable fields for insertion of the appropriate names and activity metric data (indicated in braces in the table below).

| Third Parties | Recipient is an Actor |
|---|---|
| {Joe} and {Sally} are on each other's heels | You and {Sally} are on each other's heels |
| {Brad} and {Abby} are neck-and-neck | You and {Abby} are neck-and-neck |
| {Abby} and {Brad} are in close competition | You and {Brad} are in close competition |
| {Brad} and {Abby} are elbow to elbow | You and {Abby} are elbow to elbow |
| {Abby} and {Brad} are in tight formation | You and {Brad} are in tight formation |
| {Brad} and {Abby} are only a few steps apart | You and {Abby} are only a few steps apart |
| {Abby} and {Brad} are all tied up | You and {Brad} are all tied up |
| {Brad} and {Abby} are too close for comfort | You and {Abby} are too close for comfort |
| Between {Joe} and {Sally} it's too close to call | Between you and {Sally} it's too close to call |
| {Joe} and {Sally} are in serious competition | You and {Sally} are in serious competition |
| {Joe} and {Sally} are in a deadlock | You and {Sally} are in a deadlock |
| It's an even match between {Joe} and {Sally} | It's an even match between you and {Sally} |
| The race is ON between {Joe} and {Sally} | The race is ON between you and {Sally} |

| Third Parties | Recipient is an Actor |
|---|---|
| It's gonna be a close call between {Joe} and {Sally} | It's gonna be a close call between you and {Sally} |
| {Joe} and {Sally} are lookin' Even Steven | You and {Sally} are lookin' Even Steven |

For example, when the activity level of an individual user is approaching that of another user, then a private notification may be provided to the individual user (e.g. "You're only 500 steps behind Abby"), but not to other users. Examples of message templates for such a scenario are listed in the table below.

Get ready to pass {Brad}
You're only {500} steps behind {Abby}
Time for a walk! Only {500} steps before you overtake {Brad}
Ready to rock? Get {500} more steps to pass {Abby}!
You're only {500} steps behind Joe! Start practicing your victory dance In a related example, a user that is about to be passed may receive a private notification (e.g. "Brad is only 500 steps behind you"). Examples of message templates for such a scenario are listed in the table below.

{Abby}'s on your tail
{Brad}'s coming to get you
{Abby}'s only {500} steps behind you
{Brad}'s catching up to you
{Abby}'s sneaking up on you In another example, a private notification may be sent in response to detection of a user being close to taking first place (or any other place) (e.g. "You're 500 steps from taking the lead today"). Examples of message templates for such a scenario are listed in the table below.

{500} more steps and you'll be blazing a trail to the winner's circle
You're making it rain! Storm your way to 1st place by taking {500} more steps
You're {500} steps from taking the lead today
Crush {500} steps to capture 1st place {500} steps to take the lead! The ball's in your court
Tired of second place? Take {500} more for the lead!
{500} more steps to jockey for first!

Further, personal achievements may be detected in the context of the group event, and related messages can be generated and sent. Examples of personal achievements include: someone making a significant change in activity level (but no change in position), someone reaching 100% of their goal today/yesterday, someone improving day over day, someone having a multi-day goal streak, etc.

In the table below, examples of message templates are provided for the scenario where someone made a significant change in their activity metric (e.g. acquiring an amount greater than a threshold amount), but no change in position.

| Third Party | Recipient is the Actor |
| --- | --- |
| Woot! {Sally} locked in {1,500} steps | Woot! You locked in {1,500} steps |
| Chalk up {1,500} more for {Abby} | You chalked up {1,500} more |
| {Brad} added another {1,500} steps | You added another {1,500} steps |
| {Abby}'s on the move! + {1,500} steps | You're on the move! + {1,500} steps |
| {Brad} added {1,500} steps for a total of {4,567} | You added {1,500} steps for a total of {4,567} |
| {Brad}'s stepping up with {1,500} more on the board | You're stepping up with {1,500} more on the board |
| Whoa! {Joe} came out of left field with {1,500} more steps | Whoa! You came out of left field with {1,500} more steps |
| {Joe} logged a whopping {1,500} steps | You logged a whopping {1,500} steps |
| {1,500} steps? {Joe} just threw it down! | {1,500} steps? You just threw it down! |
| Jolly good work to {Sally} for those {1,500} steps | Jolly good work for those {1,500} steps |
| Sweet mother of pearl! {Sally} added {1,500} more steps! | Sweet mother of pearl! You added {1,500} more steps! |
| {1,500} steps, {Joe}'s off and running! | {1,500} steps, you're off and running! |

In the table below, examples of message templates are provided for the scenario where someone reached 100% of their goal today.

| Third Party | Recipient is the Actor |
| --- | --- |
| {Joe} crushed it! That step goal didn't even see it coming | You crushed it! That step goal didn't even see it coming |
| {Joe} did it! Step goal met | You did it! Step goal met |
| {Brad}'s on point. {10,000} steps for the day | You're on point. {10,000} steps for the day |
| {Abby} just hit {10,000} steps. Goal complete! | You just hit {10,000} steps. Goal complete! |
| Game, Step, Match! {Joe} beat today's step goal! | Game, Step, Match! You beat today's step goal! |
| Cue the fireworks, {Joe}'s rocking the step goal | Cue the fireworks, you're rocking the step goal |
| {10,000} steps for {Brad} today. KABOOM! | {10,000} steps for you today. KABOOM! |
| {Abby}'s step goal is toast Goal complete. Three cheers for {Joe}! | That step goal of yours is toast Your goal is complete. Three cheers! |
| That step goal was no match for {Joe}! | That step goal was no match for you! |

In the table below, examples of message templates are provided for the scenario where someone reached 100% of their goal yesterday.

| Third Party | You're the Actor |
| --- | --- |
| {Joe} crushed it yesterday! That step goal didn't even see it coming | You crushed it yesterday! That step goal didn't even see it coming |
| {Brad}'s was on point yesterday. {10,000} steps for the day | You were on point yesterday. {10,000} steps for the day |
| {Abby} hit {10,000} steps yesterday. Goal complete! | You hit {10,000} steps yesterday. Goal complete! |
| {10,000} steps for {Brad} yesterday. WAHOO! | {10,000} steps for you yesterday. WAHOO! |
| That step goal yesterday was no match for {Joe}! | That step goal yesterday was no match for you! |

In the table below, examples of message templates are provided for the scenario where somebody improved day over day.

| Third Party | You're the Actor |
| --- | --- |
| {subject} really stepped up yesterday! | You really stepped up yesterday! |
| {value} % more steps than the day before | {value} % more steps than the day before |
| A {value} % improvement from $subject$ yesterday! | You made a {value} % improvement yesterday! |
| Props to {subject} for the {value} % boost yesterday | Props for the {value} % boost yesterday |
| {subject} pumped up the steps by {value} % yesterday | You pumped up the steps by {value} % yesterday |
| {subject}'s step count went up {value} % day-over-day | Your step count went up {value} % day-over-day |

In the table below, examples of message templates are provided for the scenario where somebody has a multi-day goal streak.

| Third Party | You're the Actor |
| --- | --- |
| {subject} hit {goal} steps for {value} days in a row! | You hit {goal} steps for {value} days in a row! |
| {value} days in a row getting {goal} steps. Well done, {subject} | {value} days in a row getting {goal} steps. Well done! |
| That's a {value} day streak for {subject} | That's a {value} day streak for you |
| How many days in a row can {subject} get {goal} steps? | How many days in a row can you get {goal} steps? |
| {value} | {value} |
| Can {subject} make it a {value + 1} goal streak today? | Can you make it a {value + 1} goal streak today? |

Though various examples of message templates have been provided herein, it should be appreciated that such are provided by way of example, and not by way of limitation.

It will be appreciated that for a given detected event, notifications may be sent to (a) an individual user, (b) to selected ones (some) of the users, or (c) to all of the participating users, depending upon various factors such as the characteristics of or type of event that is detected, the identities of the users that are involved in or affected by the event, the current activity state of a given user, a calendar of a user, a location of a user, time of day, etc.

For example, in some implementations, all participating users receive notifications about changes in the first place ranking; whereas notifications about other rank changes (not affecting first place) are sent to only those users who are involved in the rank change (e.g. the users whose rankings have changed). In this manner, notifications are limited so that users do not receive too many notifications. It should be appreciated that though rank changes have generally been described with reference to two users (one user passing another), there may be situations where rank changes affect more than two users (e.g. a user passes two or more users).

In some implementations, when a passing event is detected which affects a ranking that is equal to or above a threshold ranking (e.g. change in first three places), then notification messages are sent to all the participating users in the group event. Whereas if a passing event is detected which affects a ranking below the threshold ranking (e.g. fourth place and below), then notification messages are not sent to all the participating users, but are sent to the users whose rankings have been affected.

Figure 13C:
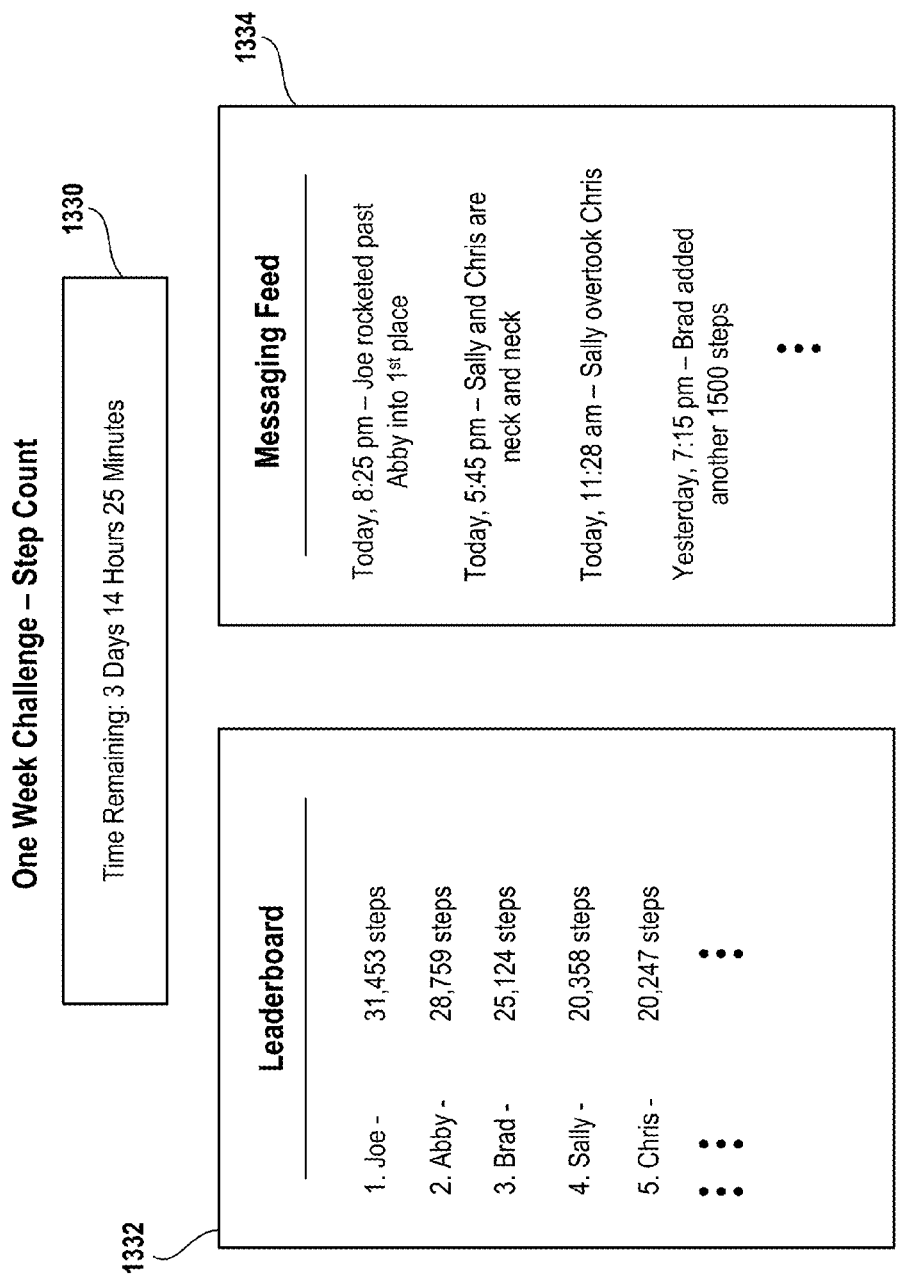
FIG. 13C illustrates an interface for displaying data pertaining to a group event, in accordance with an embodiment of the invention.

FIG. 13C illustrates an interface for displaying data pertaining to a group event, in accordance with an embodiment of the invention. In the illustrated embodiment, a one week challenge/race to determine who can achieve the highest stepcount is shown. A time remaining field 1330 is provided to display the amount of time remaining before the challenge is complete. A leaderboard 1332 lists the participating users and their associated stepcounts in a ranked order from highest to lowest. A messaging feed 1334 displays messages which have been generated for the group event. Messages may be generated automatically by the system upon detection of interesting activity as described herein. It will be appreciated that the messages appearing in the feed may be customized based on the user that is currently viewing the feed, so as to be contextually relevant to the current user, as described elsewhere herein. Furthermore, though examples of messages relating to significant activity between two users have been described, the messages can relate to any of the types of interesting/unusual activity described elsewhere herein.

Messages may also be posted by users to the messaging feed. Indeed, the messaging stemming from the automated detection of interesting activity occurring during the group event may encourage the participant users to interact more and post additional messages to the group messaging feed.

As has been noted, messages may be sent to one, some or all of the participant users. A message may appear in the messaging feed 1334, though a given user may or may not have received a notification containing the message. For example, in the implementation described above wherein notifications regarding changes in rank other than first place are sent only to those users involved, appropriate messages for the change in rank may appear in the message feed provided to other users, notwithstanding that they did not receive a notification. In this manner, the other users have access to the complete messaging activity history when accessing the message feed, but receive notifications selectively so as not to be overwhelmed with excessive notifications.

Additionally, users may cheer, taunt, and otherwise respond to specific messages.

Figure 13D:
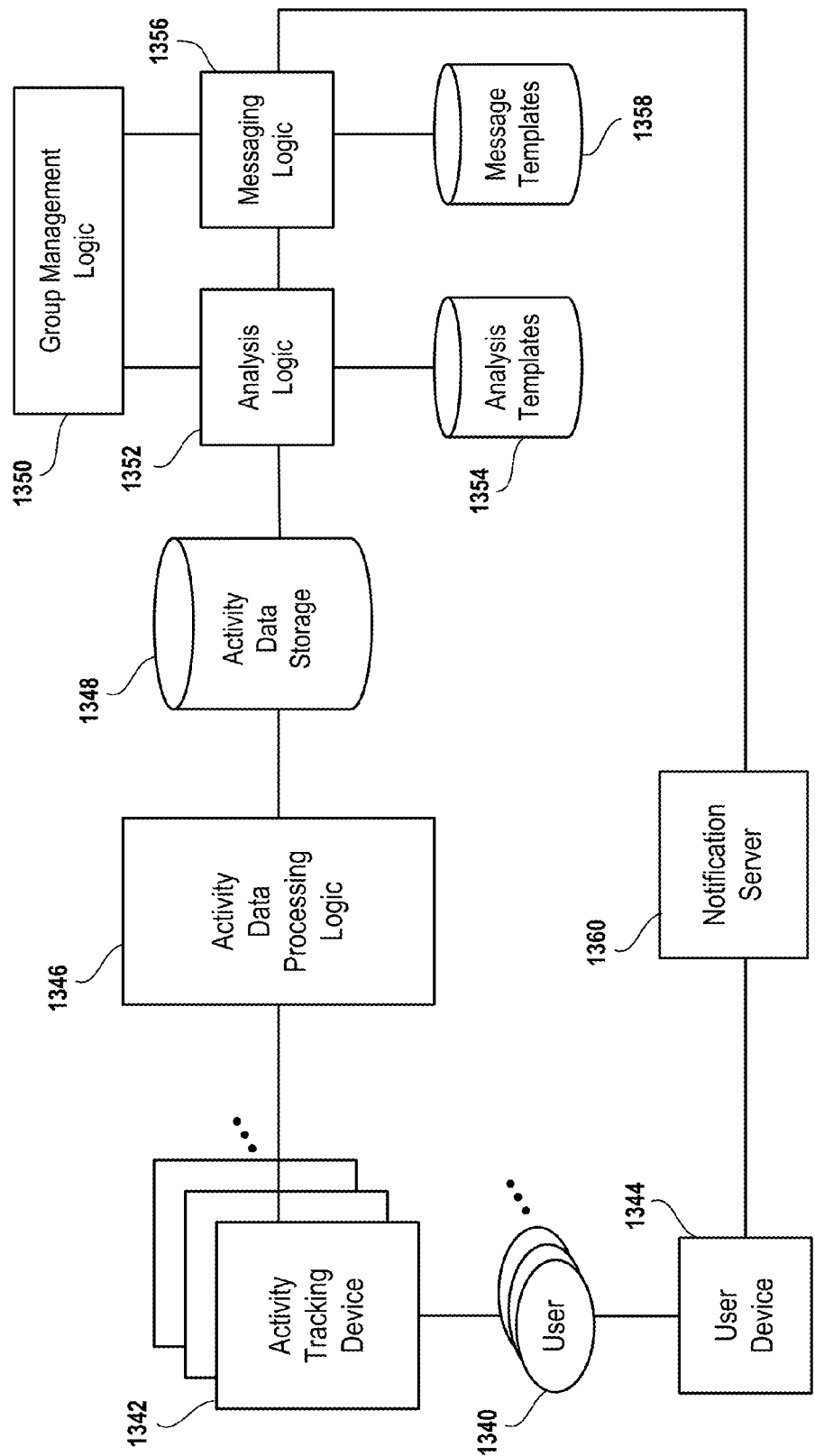
FIG. 13D illustrates a system for providing notifications to a user device, in accordance with an embodiment of the invention.

FIG. 13D illustrates a system for providing notifications to a user device, in accordance with an embodiment of the invention. An activity tracking device 1342 is associated with a user 1340. Activity data processing logic 1346 processes data from the activity tracking device 1342 for storage to an activity data storage 1348. Analysis logic 1352 is configured to analyze activity data for the user 1340, to identify interesting or unusual activity. The analysis logic 1352 may employ various analysis templates 1354 to identify the interesting or unusual activity. In response to detection of the unusual activity, messaging logic 1356 is invoked to generate a message for sending to the user. The messaging logic 1356 may be configured to select an appropriate message template from message templates 1358, based on the specific nature of the unusual activity, and populate the selected message template with customized text, including relevant activity metric data that is descriptive of the unusual activity.

The generated message can be sent via a notification server 1360, to a user device 1344 that is associated to the user 1340. Upon receipt, the message is surfaced as a notification on the user device 1344.

In another implementation, the message may be sent to and surfaced on the activity tracking device 1342.

For a group event, there may be additional users, with additionally associated activity tracking devices and user devices. Group management logic 1350 is configured to manage the formation and maintenance of a group event. Group management logic 1350 may invoke analysis logic 1352 to identify interesting activity occurring during the group event, and messaging logic 1356 to generate messages which are descriptive of the interesting activity.

In other implementations, notifications and/or messages may be processed and sent to users based other measurable or quantifiable data. For instance, instead of just using activity metrics to determine differences, changes, or relationships among one or more users, other types of data can include a user's weight (e.g., weight loss, weight gain, weight goals, weight loss competitions, weight loss challenges, etc.), a user's food intake (e.g., number of calories consumed, calorie intake per day or period of time, types of foods eaten, meals logged, meals cooked, meals shared, recipes shared, food data shared, etc.), sleep data (e.g., hours slept, number of times moved during a period of time, number of wakeups, activity during sleep periods, restful sleep periods, challenges regarding sleep metrics, etc.). It should be appreciated that these are just some examples of data that can be shared, used or consumed to enable smart notifications or messages to users or to groups of users.

Such data may be detected by, obtained or derived from sources other than the aforementioned activity tracking device, such as by user entry and/or from other types of devices. For example, in implementations wherein users' weights are tracked, weight information may be obtained through user entry (e.g. via an app on a user's mobile device, via a web interface, any other computing device), or from a scale that communicates weight information (e.g. the ARIA™ WIFI SMART SCALE sold by Fitbit Inc.). Notifications may also be surfaced on the scale. In some embodiments, notifications are displayed on the scale at the time that a user activates or otherwise uses the scale.

Figure 14:
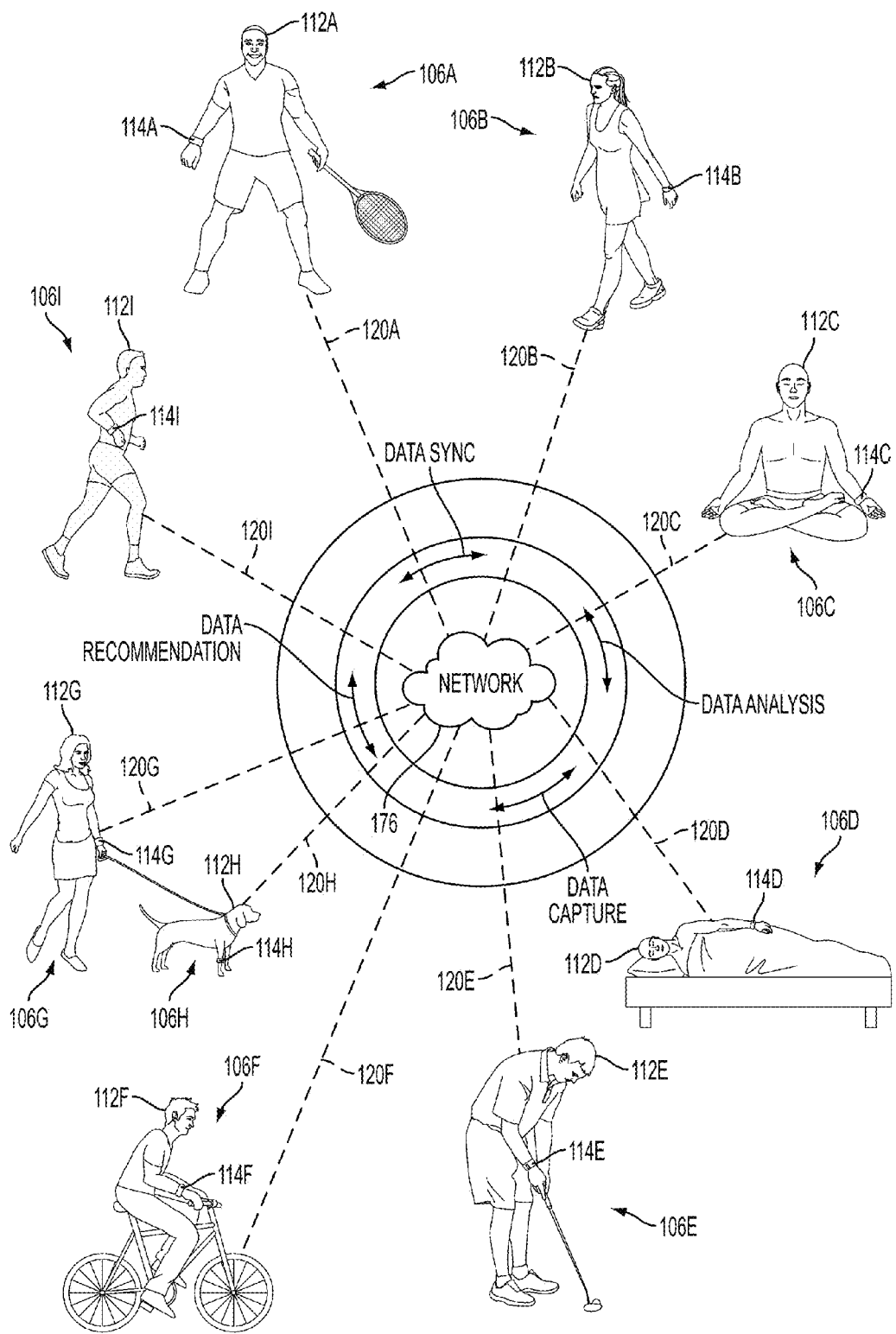
FIG. 14 illustrates an example where various types of activities of users can be captured or collected by activity tracking devices, in accordance with various embodiments of the present invention.

FIG. 14 illustrates an example where various types of activities of users 1400A-1400I can be captured by activity tracking devices 100, in accordance with one embodiment of the present invention. As shown, the various types of activities can generate different types of data that can be captured by the activity tracking device 100. The data, which can be represented as motion data (or processed motion data) can be transferred 1420 to a network 160 for processing and saving by a server, as described above. In one embodiment, the activity tracking device 100 can communicate to a device using a wireless connection, and the device is capable of communicating and synchronizing the captured data with an application running on the server. In one embodiment, an application running on a local device, such as a smart phone or tablet or smart watch can capture or receive data from the activity tracking device 100 and represent the tracked motion data in a number of metrics.

In one embodiment, the device collects one or more types of physiological and/or environmental data from embedded sensors and/or external devices and communicates or relays such metric information to other devices, including devices capable of serving as Internet-accessible data sources, thus permitting the collected data to be viewed, for example, using a web browser or network-based application. For example, while the user is wearing an activity tracking device, the device may calculate and store the user's step count using one or more sensors. The device then transmits data representative of the user's step count to an account on a web service, computer, mobile phone, or health station where the data may be stored, processed, and visualized by the user. Indeed, the device may measure or calculate a plurality of other physiological metrics in addition to, or in place of, the user's step count.

Some physiological metrics include, but are not limited to, energy expenditure (for example, calorie burn), floors climbed and/or descended, heart rate, heart rate variability, heart rate recovery, location and/or heading (for example, through GPS), elevation, ambulatory speed and/or distance traveled, swimming lap count, bicycle distance and/or speed, blood pressure, blood glucose, skin conduction, skin and/or body temperature, electromyography, electroencephalography, weight, body fat, caloric intake, nutritional intake from food, medication intake, sleep periods (i.e., clock time), sleep phases, sleep quality and/or duration, pH levels, hydration levels, and respiration rate. The device may also measure or calculate metrics related to the environment around the user such as barometric pressure, weather conditions (for example, temperature, humidity, pollen count, air quality, rain/snow conditions, wind speed), light exposure (for example, ambient light, UV light exposure, time and/or duration spent in darkness), noise exposure, radiation exposure, and magnetic field.

Still further, other metrics can include, without limitation, calories burned by a user, weight gained by a user, weight lost by a user, stairs ascended, e.g., climbed, etc., by a user, stairs descended by a user, steps taken by a user during walking or running, a number of rotations of a bicycle pedal rotated by a user, sedentary activity data, driving a vehicle, a number of golf swings taken by a user, a number of forehands of a sport played by a user, a number of backhands of a sport played by a user, or a combination thereof. In some embodiments, sedentary activity data is referred to herein as inactive activity data or as passive activity data. In some embodiments, when a user is not sedentary and is not sleeping, the user is active. In some embodiments, a user may stand on a monitoring device that determines a physiological parameter of the user. For example, a user stands on a scale that measures a weight, a body fat percentage, a biomass index, or a combination thereof, of the user.

Furthermore, the device or the system collating the data streams may calculate metrics derived from this data. For example, the device or system may calculate the user's stress and/or relaxation levels through a combination of heart rate variability, skin conduction, noise pollution, and sleep quality. In another example, the device or system may determine the efficacy of a medical intervention (for example, medication) through the combination of medication intake, sleep and/or activity data. In yet another example, the device or system may determine the efficacy of an allergy medication through the combination of pollen data, medication intake, sleep and/or activity data. These examples are provided for illustration only and are not intended to be limiting or exhaustive.

This information can be associated to the users account, which can be managed by an activity management application on the server. The activity management application can provide access to the users account and data saved thereon. The activity manager application running on the server can be in the form of a web application. The web application can provide access to a number of websites screens and pages that illustrate information regarding the metrics in various formats. This information can be viewed by the user, and synchronized with a computing device of the user, such as a smart phone.

In one embodiment, the data captured by the activity tracking device 100 is received by the computing device, and the data is synchronized with the activity measured application on the server. In this example, data viewable on the computing device (e.g. smart phone) using an activity tracking application (app) can be synchronized with the data present on the server, and associated with the user's account. In this way, information entered into the activity tracking application on the computing device can be synchronized with application illustrated in the various screens of the activity management application provided by the server on the website.

The user can therefore access the data associated with the user account using any device having access to the Internet. Data received by the network 176 can then be synchronized with the user's various devices, and analytics on the server can provide data analysis to provide recommendations for additional activity, and or improvements in physical health. The process therefore continues where data is captured, analyzed, synchronized, and recommendations are produced. In some embodiments, the captured data can be itemized and partitioned based on the type of activity being performed, and such information can be provided to the user on the website via graphical user interfaces, or by way of the application executed on the users smart phone (by way of graphical user interfaces).

In an embodiment, the sensor or sensors of a device 100 can determine or capture data to determine an amount of movement of the monitoring device over a period of time. The sensors can include, for example, an accelerometer, a magnetometer, a gyroscope, or combinations thereof. Broadly speaking, these sensors are inertial sensors, which capture some movement data, in response to the device 100 being moved. The amount of movement (e.g., motion sensed) may occur when the user is performing an activity of climbing stairs over the time period, walking, running, etc. The monitoring device may be worn on a wrist, carried by a user, worn on clothing (using a clip, or placed in a pocket), attached to a leg or foot, attached to the user's chest, waist, or integrated in an article of clothing such as a shirt, hat, pants, blouse, glasses, and the like. These examples are not limiting to all the possible ways the sensors of the device can be associated with a user or thing being monitored.

In other embodiments, a biological sensor can determine any number of physiological characteristics of a user. As another example, the biological sensor may determine heart rate, a hydration level, body fat, bone density, fingerprint data, sweat rate, and/or a bioimpedance of the user. Examples of the biological sensors include, without limitation, a biometric sensor, a physiological parameter sensor, a pedometer, or a combination thereof.

In some embodiments, data associated with the user's activity can be monitored by the applications on the server and the users device, and activity associated with the user's friends, acquaintances, or social network peers can also be shared, based on the user's authorization. This provides for the ability for friends to compete regarding their fitness, achieve goals, receive badges for achieving goals, get reminders for achieving such goals, rewards or discounts for achieving certain goals, etc.

As noted, an activity tracking device 100 can communicate with a computing device (e.g., a smartphone, a tablet computer, a desktop computer, or computer device having wireless communication access and/or access to the Internet). The computing device, in turn, can communicate over a network, such as the Internet or an Intranet to provide data synchronization. The network may be a wide area network, a local area network, or a combination thereof. The network may be coupled to one or more servers, one or more virtual machines, or a combination thereof. A server, a virtual machine, a controller of a monitoring device, or a controller of a computing device is sometimes referred to herein as a computing resource. Examples of a controller include a processor and a memory device.

In one embodiment, the processor may be a general purpose processor. In another embodiment, the processor can be a customized processor configured to run specific algorithms or operations. Such processors can include digital signal processors (DSPs), which are designed to execute or interact with specific chips, signals, wires, and perform certain algorithms, processes, state diagrams, feedback, detection, execution, or the like. In some embodiments, a processor can include or be interfaced with an application specific integrated circuit (ASIC), a programmable logic device (PLD), a central processing unit (CPU), or a combination thereof, etc.

In some embodiments, one or more chips, modules, devices, or logic can be defined to execute instructions or logic, which collectively can be viewed or characterized to be a processor. Therefore, it should be understood that a processor does not necessarily have to be one single chip or module, but can be defined from a collection of electronic or connecting components, logic, firmware, code, and combinations thereof.

Examples of a memory device include a random access memory (RAM) and a read-only memory (ROM). A memory device may be a Flash memory, a redundant array of disks (RAID), a hard disk, or a combination thereof.

Embodiments described in the present disclosure may be practiced with various computer system configurations including hand-held devices, microprocessor systems, microprocessor-based or programmable consumer electronics, minicomputers, mainframe computers and the like. Several embodiments described in the present disclosure can also be practiced in distributed computing environments where tasks are performed by remote processing devices that are linked through a wire-based or wireless network.

With the above embodiments in mind, it should be understood that a number of embodiments described in the present disclosure can employ various computer-implemented operations involving data stored in computer systems. These operations are those requiring physical manipulation of physical quantities. Any of the operations described herein that form part of various embodiments described in the present disclosure are useful machine operations. Several embodiments described in the present disclosure also relate to a device or an apparatus for performing these operations. The apparatus can be specially constructed for a purpose, or the apparatus can be a computer selectively activated or configured by a computer program stored in the computer. In particular, various machines can be used with computer programs written in accordance with the teachings herein, or it may be more convenient to construct a more specialized apparatus to perform the required operations.

Various embodiments described in the present disclosure can also be embodied as computer-readable code on a non-transitory computer-readable medium. The computer-readable medium is any data storage device that can store data, which can thereafter be read by a computer system. Examples of the computer-readable medium include hard drives, network attached storage (NAS), ROM, RAM, compact disc-ROMs (CD-ROMs), CD-recordables (CD-Rs), CD-rewritables (RWs), magnetic tapes and other optical and non-optical data storage devices. The computer-readable medium can include computer-readable tangible medium distributed over a network-coupled computer system so that the computer-readable code is stored and executed in a distributed fashion.

Although the method operations were described in a specific order, it should be understood that other housekeeping operations may be performed in between operations, or operations may be performed in an order other than that shown, or operations may be adjusted so that they occur at slightly different times, or may be distributed in a system which allows the occurrence of the processing operations at various intervals associated with the processing.

Although the foregoing embodiments have been described in some detail for purposes of clarity of understanding, it will be apparent that certain changes and modifications can be practiced within the scope of the appended claims. Accordingly, the present embodiments are to be considered as illustrative and not restrictive, and the various embodiments described in the present disclosure are not to be limited to the details given herein, but may be modified within the scope and equivalents of the appended claims.

What is claimed is:

1. A system comprising at least one server computer having at least one processor programmed to:
receive, over a network, activity data of a first user measured by an activity monitoring device;
process the activity data of the first user to update a value of an activity metric for the first user;
responsive to updating the value of the activity metric for the first user, identify a change in an inequality relationship between the value of the activity metric for the first user and a value of the activity metric for a second user, the change in the inequality relationship being defined by the value of the activity metric for the first user changing, from being less than the value of the activity metric for the second user, to being greater than the value of the activity metric for the second user; and
responsive to identifying the change in the inequality relationship, trigger, over the network, a first user device to prompt the first user to generate a message to the second user for display on a second user device.

2. The system of claim 1, wherein the inequality relationship between the value of the activity metric for the first user and the value of the activity metric for the second user defines a relative ranking of the first user and the second user on a competitive leaderboard for the activity metric.

3. The system of claim 2, wherein the change in the inequality relationship defines a change in the relative ranking of the first user and the second user on the competitive leaderboard for the activity metric.

4. The system of claim 3, wherein the triggering of the first user device to prompt the first user to generate a message includes identifying the change in the relative ranking of the first user and the second user.

5. The system of claim 1, wherein the triggering of the first user device to prompt the first user to generate a message to the second user includes triggering a notification to the first user, the notification providing access to an interface configured to receive input from the first user to define content of the message to the second user.

6. The system of claim 5, wherein the notification is a push notification to a mobile device.

7. The system of claim 5, wherein the interface provides at least one option to send a predefined message to the second user.

8. The system of claim 1, wherein the activity metric is defined by one or more of the following: stepcount, elevation climbed, distance traveled, active amount of time.

9. A system comprising at least one server computer having at least one processor programmed to:
receive, over a network, activity data of a first user measured by an activity monitoring device;
process the activity data of the first user to update a value of an activity metric for the first user;
responsive to updating the value of the activity metric for the first user, identify a change in an inequality relationship between the value of the activity metric for the first user and a value of the activity metric for a second user, the change in the inequality relationship being defined by the value of the activity metric for the first user changing, from being greater than the value of the activity metric for the second user, to being less than the value of the activity metric for the second user; and
responsive to identifying the change in the inequality relationship, trigger, over the network, a first user device to prompt the first user to generate a message to the second user for display on a second user device.

10. The system of claim 9, wherein the inequality relationship between the value of the activity metric for the first user and the value of the activity metric for the second user defines a relative ranking of the first user and the second user on a competitive leaderboard for the activity metric.

11. The system of claim 10, wherein the change in the inequality relationship defines a change in the relative ranking of the first user and the second user on the competitive leaderboard for the activity metric.

12. The system of claim 11, wherein the triggering of the first user device to prompt the first user to generate a message includes identifying the change in the relative ranking of the first user and the second user.

13. The system of claim 9, wherein the triggering of the first user device to prompt the first user to generate a message to the second user includes triggering a notification to the first user, the notification providing access to an interface configured to receive input from the first user to define content of the message to the second user.

14. The system of claim 13, wherein the notification is a push notification to a mobile device.

15. The system of claim 13, wherein the interface provides at least one option to send a predefined message to the second user.

16. The system of claim 9, wherein the activity metric is defined by one or more of the following: stepcount, elevation climbed, distance traveled, active amount of time.

17. A system comprising at least one server computer having at least one processor programmed to:
process requests, received over a network from a plurality of client devices, for a plurality of users to join a group event, the group event defined for an activity metric for each of the plurality of users for a period of time;
process activity data, received over the network, associated with each of the plurality of users during the period of time to track the activity metric for each of the plurality of users, the activity data for a given user being determined from motion data detected by an activity monitoring device associated with the given user;
analyze the activity metrics of the plurality of users to determine a ranking of the plurality of users based on their activity metrics, and to identify a change in relationship between activity metrics of two or more of the plurality of users, the change in relationship being defined by an activity metric of a first one of the users surpassing an activity metric of a second one of the users by at least a predefined amount;
responsive to identifying the change in relationship, identify one or more user accounts of select ones of the plurality of users, select a message template based on the identified change in relationship, and populate the message template to generate a message describing the change in relationship; and
send the message over the network to one or more of the client devices associated with the one or more user accounts for display thereon.

18. The system of claim 17, wherein when the identified change in relationship affects a position in the ranking that is equal to or higher than a threshold position, then the select ones of the plurality of users to receive the message are defined by all of the plurality of users.

19. The system of claim 18, wherein when the identified change in relationship affects a position in the ranking that is less than the threshold position, then the select ones of the plurality of users to receive the message are defined by the two or more of the plurality of users for whom the change in relationship is identified.

20. The system of claim 17, wherein the group event defines one of a competitive race for the plurality of users, a common goal for each of the plurality of users, or a collective goal for the plurality of users.

21. The system of claim 17, wherein sending the message is defined by one or more of a push notification, a private message, or an e-mail.

22. The system of claim 17, wherein selecting the message template is based on the identified one or more user accounts of the select ones of the plurality of users.

23. The system of claim 17, wherein the select ones of the plurality of users to receive the message are defined by one, or two, or some, or all of the plurality of users, that are selected based on characteristics of the change in the relationship between activity metrics of the two or more of the plurality of users.

24. The system of claim 17, wherein populating the message template is defined by insertion of custom text that is based on activity metrics of the two or more users for whom the change in relationship is identified.

25. The system of claim 17, wherein the message is displayed as part of a message feed defined for the group event.

26. A system comprising at least one server computer having at least one processor programmed to:
process requests, received over a network from a plurality of client devices, for a plurality of users to join a group event, the group event defined for an activity metric for each of the plurality of users for a period of time;
process activity data, received over the network, associated with each of the plurality of users during the period of time to track the activity metric for each of the plurality of users, the activity data for a given user being determined from motion data detected by an activity monitoring device associated with the given user;
analyze the activity metrics of the plurality of users to determine a ranking of the plurality of users based on their activity metrics, and to identify a change in relationship between activity metrics of two or more of the plurality of users, the change in relationship being defined by an activity metric of a first one of the users surpassing an activity metric of a second one of the users by less than a predefined amount;

responsive to identifying the change in relationship, identify one or more user accounts of select ones of the plurality of users, select a message template based on the identified change in relationship, and populate the message template to generate a message describing the change in relationship; and send the message over the network to one or more of the client devices associated with the one or more user accounts for display thereon.

27. The system of claim 26, wherein when the identified change in relationship affects a position in the ranking that is equal to or higher than a threshold position, then the select ones of the plurality of users to receive the message are defined by all of the plurality of users.

28. The system of claim 27, wherein when the identified change in relationship affects a position in the ranking that is less than the threshold position, then the select ones of the plurality of users to receive the message are defined by the two or more of the plurality of users for whom the change in relationship is identified.

29. The system of claim 26, wherein sending the message is defined by one or more of a push notification, a private message, or an e-mail.

30. The system of claim 26, wherein populating the message template is defined by insertion of custom text that is based on activity metrics of the two or more users for whom the change in relationship is identified.

* * * * *